(12) United States Patent
Ryan

(10) Patent No.: US 10,172,709 B2
(45) Date of Patent: Jan. 8, 2019

(54) DELIVERY SYSTEMS AND METHODS OF IMPLANTATION FOR REPLACEMENT PROSTHETIC HEART VALVE

(71) Applicant: Medtronic, Inc., Minneapolis, MN (US)

(72) Inventor: Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 270 days.

(21) Appl. No.: 15/181,695

(22) Filed: Jun. 14, 2016

(65) Prior Publication Data

US 2016/0367362 A1 Dec. 22, 2016

Related U.S. Application Data

(63) Continuation of application No. 14/097,552, filed on Dec. 5, 2013, now Pat. No. 9,370,423, which is a continuation of application No. 12/070,380, filed on Feb. 15, 2008, now Pat. No. 8,623,074.

(60) Provisional application No. 60/901,787, filed on Feb. 16, 2007.

(51) Int. Cl.
*A61F 2/24* (2006.01)
*A61F 2/958* (2013.01)

(52) U.S. Cl.
CPC .......... *A61F 2/2418* (2013.01); *A61F 2/2409* (2013.01); *A61F 2/2433* (2013.01); *A61F 2/2436* (2013.01); *A61F 2/24* (2013.01); *A61F 2/958* (2013.01); *A61F 2210/0014* (2013.01); *A61F 2220/005* (2013.01); *A61F 2220/0075* (2013.01); *A61F 2230/0054* (2013.01);
(Continued)

(58) Field of Classification Search
CPC .... A61F 2/2418; A61F 2/2409; A61F 2/2436; A61F 2/2433; A61F 2220/0075; A61F 2310/00023; A61F 2/24; A61F 2210/0014; A61F 2230/0069; A61F 2220/005; A61F 2230/0054; A61F 2/958
See application file for complete search history.

(56) References Cited

U.S. PATENT DOCUMENTS

| 7,399,315 | B2 | 7/2008 | Iobbi |
| 7,556,646 | B2 | 7/2009 | Yang et al. |
| 7,806,927 | B2 | 10/2010 | Styrc |

(Continued)

FOREIGN PATENT DOCUMENTS

| EP | 1671608 | | 6/2006 |
| EP | 3111888 | A1 | 1/2017 |

(Continued)

OTHER PUBLICATIONS

Boudjemline, et al., "New insights in minimally invasive valve replacement: description of a cooperative approach for the off-pump replacement of mitral valves," European Heart Journal (2005) 26, 2013-2017.

(Continued)

*Primary Examiner* — Julian W Woo
(74) *Attorney, Agent, or Firm* — Dicke, Billig & Czaja, PLLC

(57) ABSTRACT

A delivery system and method for positioning and partially deploying a replacement valve at an implantation site, verifying the location of the replacement valve relative to the implantation site, and retrieving the partially deployed stent for repositioning relative to the implantation site.

18 Claims, 21 Drawing Sheets

(52) U.S. Cl.
CPC ............. *A61F 2230/0069* (2013.01); *A61F 2310/00023* (2013.01)

(56) References Cited

U.S. PATENT DOCUMENTS

| | | |
|---|---|---|
| 7,959,666 B2 | 6/2011 | Salahieh |
| 2005/0137682 A1 | 6/2005 | Justino |
| 2006/0074484 A1 | 4/2006 | Huber |
| 2006/0149360 A1 | 7/2006 | Schwammenthal et al. |

FOREIGN PATENT DOCUMENTS

| | | |
|---|---|---|
| FR | 2874812 A1 | 3/2006 |
| WO | WO07/013999 | 2/2007 |
| WO | WO07/071436 | 6/2007 |

OTHER PUBLICATIONS

Walther, et al., "Valve-in-a-Valve Concept for Transcatheter Minimally Invasive Repeat Xenograft Implantation," JACC, vol. 50, No. 1, 2007, Jul. 3, 2007:56-60.

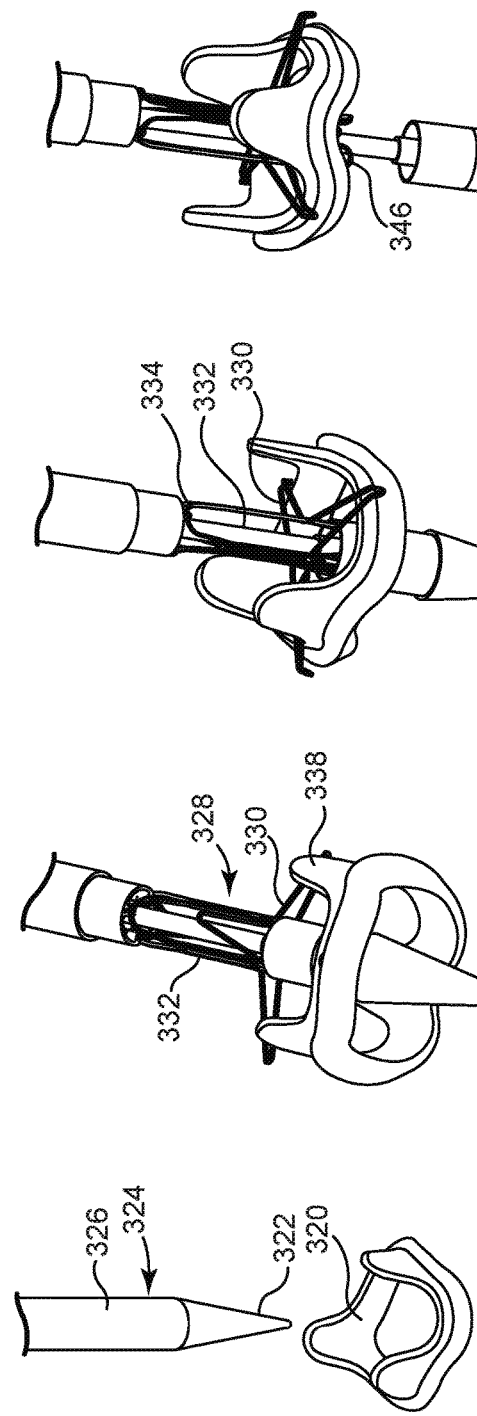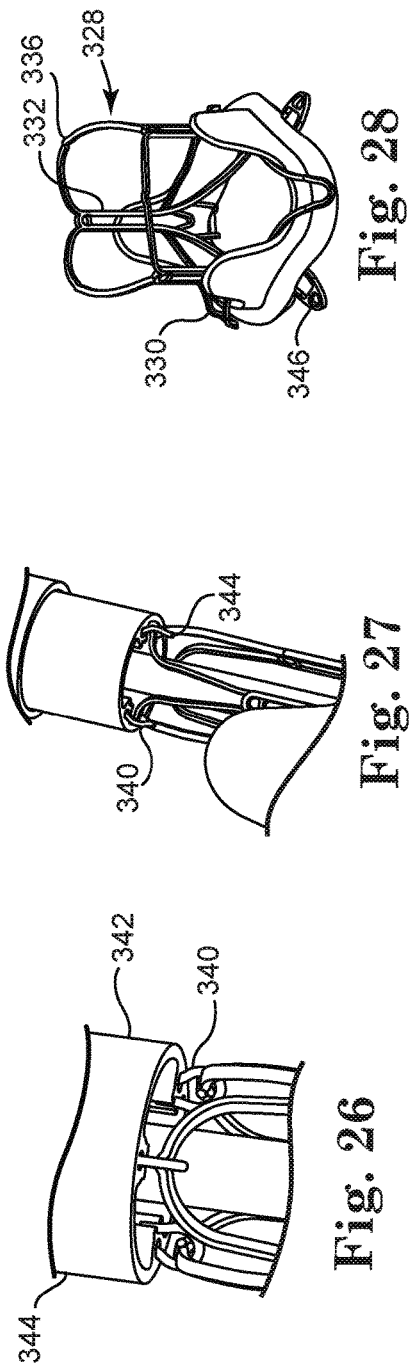

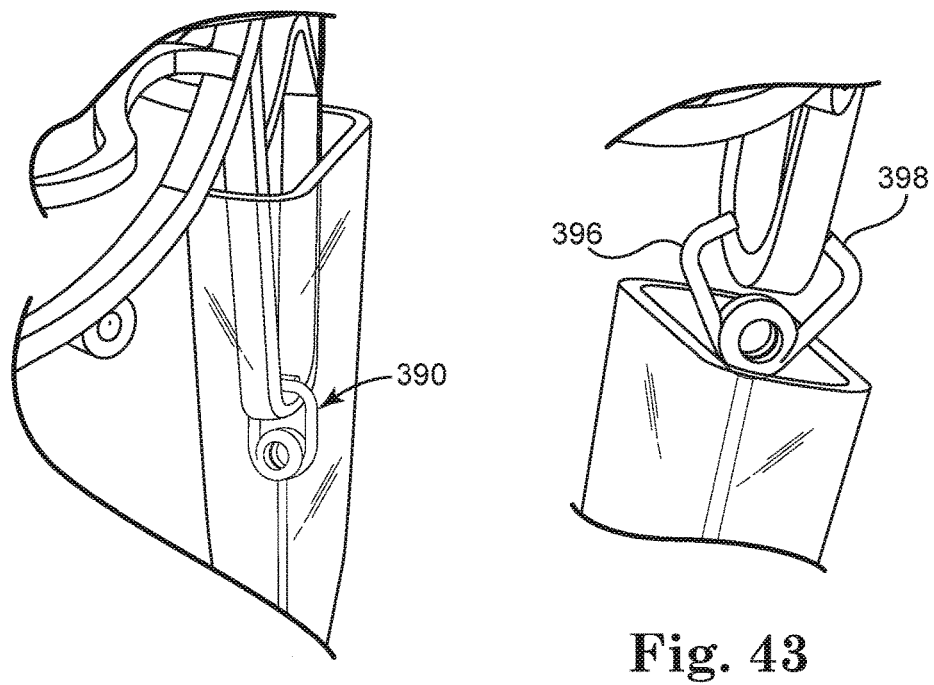
Fig. 42
Fig. 43
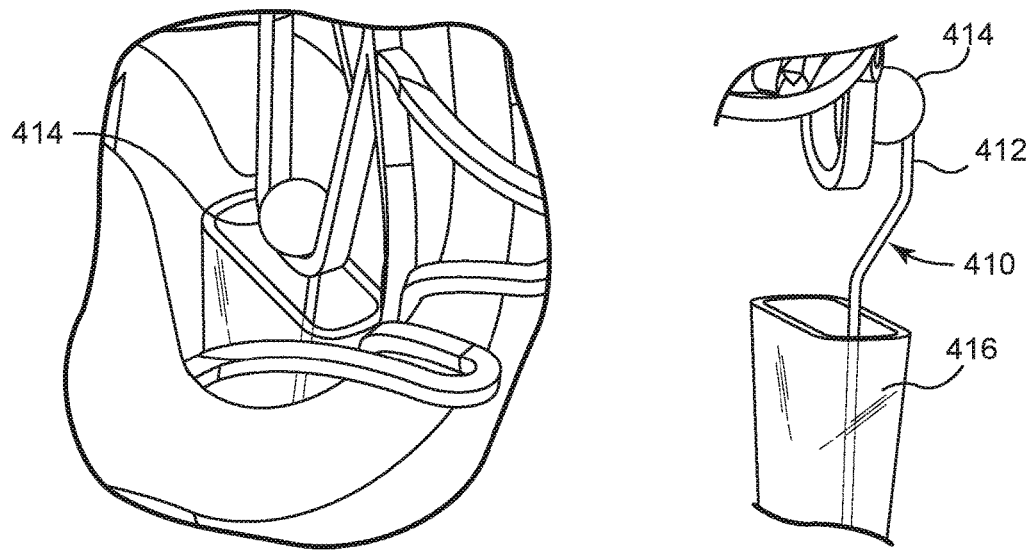
Fig. 44
Fig. 45

DELIVERY SYSTEMS AND METHODS OF IMPLANTATION FOR REPLACEMENT PROSTHETIC HEART VALVE

CROSS-REFERENCE TO RELATED APPLICATION

The present application is a Continuation of and claims priority to U.S. patent application Ser. No. 14/097,552, filed Dec. 5, 2013, now U.S. Pat. No. 9,370,423, which is a Continuation of and claims priority to U.S. patent application Ser. No. 12/070,380, filed Feb. 15, 2008, now U.S. Pat. No. 8,623,074, which claims priority to U.S. Provisional Application No. 60/901,787, filed Feb. 16, 2007 the entire contents of which is incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Various types and configurations of prosthetic heart valves are used to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses.

As used throughout this specification a "prosthetic heart valve" is intended to encompass bioprosthetic heart valves having leaflets made of a biological material (e.g., harvested porcine valve leaflets, or bovine or equine pericardial leaflets), along with synthetic leaflet materials or other materials. These bioprosthetic heart valves typically include a stent having a substantially circular base (or stent ring), around which an annular suture material is disposed for suturing the prosthesis to heart tissue. The stent further typically includes at least two, but typically three, support structures extending from the stent ring. These support structures are commonly referred to as stent posts or commissure posts. These posts typically are rigid yet somewhat flexible structures extending from the stent ring, which are covered by a cloth-like material similar to that of the annular suture material. The stent or commissure posts define the juncture between adjacent tissue or synthetic leaflets otherwise secured thereto. Examples of bioprosthetic heart valves are described in U.S. Pat. No. 4,106,129 (Carpentier et al.), and U.S. Pat. No. 5,037,434 (Lane), the entire disclosures of which are incorporated herein by reference. These disclosures describe a conventional configuration of three leaflets, with one leaflet disposed between each pair of stent or commissure posts. Regardless of whether a stent is provided, however, bioprosthetic heart valves are generally tubular so that when the leaflets are in an open position, an internal passage is defined through which blood can flow.

The bioprosthetic heart valves further typically include a sewing ring or suture ring that provides a means for fixing the prosthetic heart valve to the patient's native heart valve orifice tissue (e.g., native annulus or valvular rim) that is associated with the native heart valve being repaired or replaced. In particular, an exacting surgical implantation technique is traditionally employed whereby the heart is stopped (i.e., cardiopulmonary bypass) and opened, which is followed by surgical removal of damaged or diseased natural valve structure. A prosthetic heart valve can then be oriented within the native valvular area, with the sewing ring being seated against or at the native annulus or valvular rim. Sutures are then used to affix the sewing ring to the natural tissue. Obviously, the risks associated with this invasive type of surgery are numerous, particularly when cardiopulmonary bypass procedures are used.

A successfully implanted prosthetic heart valve will normally function without problems for many years. In certain instances, however, deficiencies may become evident shortly after implant or within a few years, particularly in younger patients. Common functional deficiencies include the calcification of the prosthetic heart valve leaflets, stenosis, and prosthetic heart valve insufficiency. Under these and other circumstances, the prosthetic heart valve does not function properly and conventionally requires surgical removal and replacement. Surgical removal of such a previously implanted prosthetic heart valve entails the same invasive surgical intervention described above, coupled with the need to remove the old prosthetic valve and implant a new prosthetic heart valve. In addition, the risk of mortality is often higher when performing a second surgery in the same area of the body, particularly when performing heart-related surgeries. Another disadvantage to this additional surgery is that the reopening of a sternotomy has been known to have a relatively high risk of causing an infection.

Thus, while these types of surgeries are well-accepted, the conventional surgical intervention described above is difficult to perform and can result in patient injury or more severe complications. In fact, due to physical weakness of a patient, implantation of a prosthetic heart valve via the conventional surgical technique may be considered too high-risk or contra-indicated for certain patients. Further, removal of a previously implanted prosthetic heart valve requires cutting of the sutures that secure the prosthesis to the native annulus/valvular rim, and attachment of a new sewing ring via stitching, which can further compromise the integrity of the valvular rim and lead to recovery complications, morbidity, and mortality.

Although not necessarily related to the specific prosthetic heart valve replacement concerns described above, efforts have also been made to devise a prosthetic heart valve capable of being delivered percutaneously via transcatheter implantation, thereby avoiding the complications and risks associated with conventional surgical intervention. For example, in U.S. Pat. No. 6,168,614 (Andersen et al.), a heart valve prosthesis is described for implantation in the body by use of a catheter. The valve prosthesis consists of a support structure with a tissue valve connected to it, whereby the support structure is delivered in a collapsed state through a blood vessel and secured to a desired valve location with the support structure in an expanded state.

Other percutaneously-delivered prosthetic heart valves have been suggested having a generally similar configuration, such as by Bonhoeffer, P. et al., "*Transcatheter Implantation of a Bovine Valve in Pulmonary Position.*" Circulation, 2002; 102:813-816, and by Cribier, A. et al. "*Percutaneous Transcatheter Implantation of an Aortic Valve Prosthesis for Calcific Aortic Stenosis.*" Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and any balloons used to expand the stent. Thus, with these transcatheter techniques, conventional sewing of the prosthetic heart valve to the patient's native tissue is not necessary. Similarly, in an article by Bonhoeffer, P. et al. titled "*Percutaneous Insertion of the Pulmonary Valve.*" J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Devices and methods have more recently been developed for percutaneously replacing deficient, previously implanted prosthetic heart valves, which are described, for example, in U.S. Patent Publication No. 2006/0052867 (Revuelta et al.), the entire disclosure of which is incorporated herein by reference. Other transcatheter technologies for delivering replacement valves are described in PCT Application Nos. WO 2007/053243-A2, WO 2007/130537-A1, and WO 2007/081820-A1; United States Patent Application Publication Nos. 2005/0251251-A1, 2007/0043435-A1, and 2008/0004696-A1; and U.S. Pat. No. 7,195,641. However, a need exists for additional delivery systems, and related methods of implanting replacement heart valves, that are conducive to percutaneous delivery for replacing a deficient, previously implanted bioprosthetic heart valve.

SUMMARY

The delivery systems of the invention can be used with a number of different configurations of replacement valves that provide complimentary features to promote physical docking or connection of the replacement heart valve to a previously implanted prosthetic heart valve, such as the aortic valve, mitral valve, pulmonic valve, and/or tricuspid valve. In some embodiments, the delivery systems and related methods of implantation of the invention utilize a previously implanted prosthetic heart valve as a platform to facilitate mounting relative to a native heart valve. Thus, the delivery systems of the invention are amenable to percutaneous delivery via either a transarterial or apical approach (either with or without cardiopulmonary bypass). Further, in cases where a previously implanted prosthetic heart valve is being functionally replaced, the deficient prosthetic heart valve need not be physically removed from the patient. Thus, the systems for delivering replacement heart valves of the present invention can be used at any point during the "useful life" of a conventional prosthetic heart valve. Further, the methodology associated with the present invention can be repeated multiple times, such that the delivery systems of the invention can be used to deliver multiple prosthetic heart valves on top of or within one another, if necessary or desired.

The delivery systems of the invention include features for engagement with a stent to which a valve structure is attached. These stents can include a wide variety of structures and features that can be used alone or in combination with features of other stents and/or heart valves. In particular, these stents provide a number of different docking and/or anchoring structures that cooperate with the structure of a previously implanted prosthetic heart valve, and are conducive to percutaneous delivery thereof. Many of the structures are thus compressible to a relatively small diameter for percutaneous delivery to the heart of the patient using the delivery systems and implantation methods of the invention, and then are expandable through another movement or action of the delivery system.

Methods for insertion of the replacement heart valves of the invention include delivery systems that can maintain the stent structures in their compressed state during their insertion and allow or cause all or specific features of the stent structures to expand once they are in their desired location. In addition, delivery methods of the invention can further include features that allow the stents to be retrieved for removal of relocation thereof after they have been deployed from the stent delivery systems. Such methods advantageously provide a surgeon with flexibility in proper placement of a heart valve within a patient. The methods may include implantation of the stent structures using either an antegrade or retrograde approach. Further, in many of the delivery approaches of the invention, the stent structure is rotatable in vivo to allow the stent structure to be positioned in a desired orientation.

BRIEF DESCRIPTION OF THE DRAWINGS

The present invention will be further explained with reference to the appended Figures, wherein like structure is referred to by like numerals throughout the several views, and wherein:

FIGS. 22-27 are multiple perspective views of sequential steps for delivering a stent to a prosthetic heart valve in accordance with the invention;

FIG. 28 is a perspective view of a prosthetic heart valve with a stent of a replacement prosthetic heart valve of the invention positioned therein;

FIGS. 42-43 are perspective views of another engagement mechanism of a delivery system as it is engaged with and released from a portion of a stent;

FIGS. 44-45 are perspective views of yet another released mechanism of a delivery system as it is engaged with and released from a portion of a stent;

DETAILED DESCRIPTION

Figure 1:
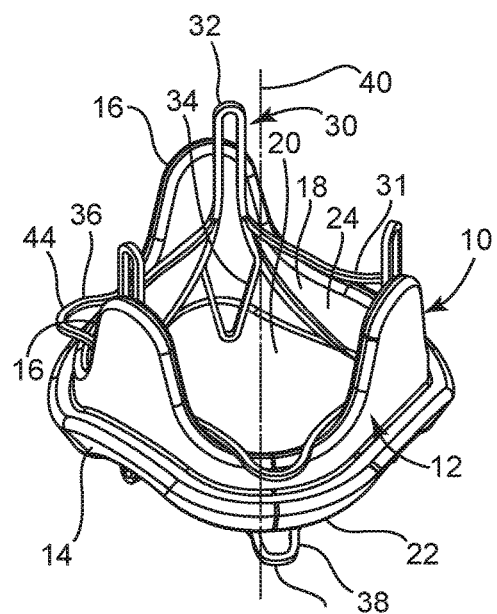
FIG. 1 is a perspective view of a prosthetic heart valve with a stent of a replacement prosthetic heart valve positioned therein.

The delivery systems and methods of the invention can be used with heart valves having a wide variety of configurations, a number of which are described below. In many cases, only the stent portion of a heart valve is illustrated, although it is understood that multiple leaflets will typically be attached within the interior portion of each stent so that it can perform as a valve. In some cases, these stents are described and illustrated as being positioned relative to a previously implanted prosthetic heart valve, where the stents can be delivered using one or more of the delivery systems and methods described herein, where many of the delivery systems can optionally be used to recapture or retrieve a stent of a heart valve after it has been at least partially deployed.

Referring now to the Figures, wherein the components are labeled with like numerals throughout the several Figures, and initially to FIG. 1, a prosthetic heart valve 10 is illustrated with a stent 30 of the invention positioned therein, which will be described in further detail below. However, referring specifically to the prosthetic heart valve 10, this valve 10 is a typical configuration of a valve that can be implanted within the heart of a patient, such as by suturing or otherwise securing the valve 10 into the area of a native heart valve of a patient. The native heart valves referred to herein can be any of the human heart valves (i.e., mitral valve, tricuspid valve, aortic valve, or pulmonary valve), wherein the type and orientation of an implanted (e.g., surgically implanted) prosthetic heart valve 10 will correspond with the particular form, shape, and function of the native heart valve in which it is implanted.

Valve 10 generally includes a valve structure 12 including a stent ring 14 from which three stent posts or commissure posts 16 extend. All or a portion of the valve structure 12, including the stent ring 14 and stent posts 16, can be covered by a flexible covering 18, which may be a tissue, polymer, fabric, cloth material, or the like to which leaflets (not shown) of the heart valve 10 are attached, such as by sewing. Further, as is known in the art, the internal structure of each of the stent posts 16 can be formed of a stiff but somewhat resiliently bendable material. This construction allows the stent posts 16 to be moved from the orientation shown in FIG. 1 to a deflected orientation by the application of an external force. Once this external force is removed or reduced, the stent posts 16 can then move back toward the orientation shown in FIG. 1.

The valve structure 12 is generally tubular in shape, defining an internal area 20 (referenced generally) that extends from an inflow end 22 to an outflow end 24. The internal area 20 is essentially surrounded by the valve structure 12, and the leaflets attached within the valve structure 12 selectively allow for fluid flow into or out of the lumen of the natural heart valve in which it is implanted. That is, the internal area 20 is alternatively open and closed to the lumen of the natural heart valve in which it is inserted via movement of leaflets. In some patients, the prosthetic heart valve 10 will have previously been implanted in a patient using typical surgical techniques, whereby the stent ring 14 is sewn or attached to the annulus or valvular rim of the native heart valve. Alternatively, the prosthetic valve could have been previously placed in the patient using minimally invasive techniques for holding the valve in place, such as U-clips, for example, or a wide variety of other techniques and features used for minimally invasive and/or percutaneous implantation of the initial prosthetic heart valve.

The prosthetic heart valves (e.g., heart valve 10) used in accordance with the delivery systems and methods of the invention may include a wide variety of different configurations, such as a prosthetic heart valve that has tissue leaflets, or a synthetic heart valve that has polymeric leaflets. In this way, the delivery systems can be used with prosthetic heart valves that are specifically configured for replacing any heart valve. That is, while much of the description herein refers to replacement of aortic valves, the delivery systems of the invention can also generally be used for replacement of tricuspid valves, delivery of venous valves, or for replacing a failed bioprosthesis, such as in the area of an aortic valve or mitral valve, for example. The delivery systems of the invention can also be used for functionally replacing stentless prosthetic heart valves.

The delivery systems of the invention are used for delivering a replacement prosthetic heart valve relative to a previously implanted prosthetic heart valve, which may be configured as the heart valve 10 shown and described herein. This would become a desirable procedure in cases where it is determined that a previously implanted prosthetic heart valve is functionally deficient due to one or more of a variety of factors, such as stenosis, valve failure, inflammation, native valve insufficiency, etc. Regardless of the cause of the deficiency, rather than removing the previously implanted prosthetic heart valve and implanting a second, similarly formed prosthetic heart valve via relatively complicated and invasive open heart surgical techniques, the delivery systems and methods of the present invention leave the deficient previously implanted prosthetic heart valve in place, and the new prosthetic heart valve is deployed so that it functionally replaces the previously implanted prosthetic heart valve. Prior to implanting the new prosthetic valve, the leaflets of the previously implanted and deficient prosthetic heart valve can either be removed using a variety of techniques such as cutters, lasers, and the like, or the leaflets may instead be left in place within the deficient valve, where they will likely be pushed toward the walls of the vessel upon implantation of the new valve.

One embodiment of a stent 30, which can be used as a component of a prosthetic heart valve in accordance with the present invention, is shown in FIG. 1. Stent 30 includes a support structure 31 comprising a number of strut or wire portions arranged relative to each other to provide secure coupling between the stent 30 and a prosthetic heart valve 10 in which it is located. In addition, stent 30 provides a semi-rigid frame for the leaflets of the replacement heart valve, which will be attached in some way within the interior portion of stent 30. Details of several configurations of the stents of the invention are described below; however, in general terms, the stents described herein are generally a series of wires arranged into a tubular support structure, and leaflets can be secured to the interior of the support structure. The leaflets can be formed from a variety of materials, such as autologous tissue, xenograph material, synthetics, or the like, as known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled and attached to a stent support structure. The support structures shown and described relative to the Figures are generally configured to accommodate three leaflets and replace a heart valve (e.g., heart valve 10) that has three commissure posts that accommodate a three-leaflet structure. However, the replacement prosthetic heart valves can incorporate more or less than three leaflets.

In more general terms, the delivery systems and methods of the invention can be used for many different devices that combine a support structure with one or more leaflets to assume configurations that differ from those shown and described, including any known prosthetic heart valve design. In one embodiment, a stent support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "*Percutaneous Insertion of the Pulmonary Valve*", Pediatric Cardiology, 2002; 39:1664-1669; Andersen H R, et al., "*Transluminal Implantation of Artificial Heart Valves*", EUR Heart J., 1992; 13:704-708; Andersen, H. R., et al., "*Transluminal Catheter Implantation of New Expandable Artificial Cardiac Valve*", EUR Heart J., 1990, 11: (Suppl) 224a; Hilbert S. L., "*Evaluation of Explanted Polyurethane Trileaflet Cardiac Valve Prosthesis*", J Thorac Cardiovascular Surgery, 1989; 94:419-29; Block P C, "*Clinical and Hemodyamic Follow-Up After Percutaneous Aortic Valvuloplasty in the Elderly*", The American Journal of Cardiology, Vol. 62, Oct. 1, 1998; Boudjemline, Y., "*Steps Toward Percutaneous Aortic Valve Replacement*", Circulation, 2002; 105:775-558; Bonhoeffer, P., "*Transcatheter Implantation of a Bovine Valve in Pulmonary Position, a Lamb Study*", Circulation, 2000:102:813-816; Boudjemline, Y., "*Percutaneous Implantation of a Valve in the Descending Aorta In Lambs*", EUR Heart J, 2002; 23:1045-1049; and Kulkinski, D., "*Future Horizons in Surgical Aortic Valve Replacement: Lessons Learned During the Early Stages of Developing a Transluminal Implantation Technique*", ASAIO J, 2004; 50:364-68).

The stent 30 comprises a support structure 31 that is made up of a number of struts or wire segments arranged to provide desired docking or engagement features, which may include individual struts or wire segments arranged and secured to each other, or the support structure 31 may instead be formed from a single piece of material (e.g., a tube of material that is machined to provide the structure shown). In FIG. 1, stent 30 is shown as being positioned within a heart valve 10, which typically would have been previously implanted in a patient. Stent 30 comprises a support structure 31 having multiple upper vertical members 32 spaced apart from each other around the perimeter of the support structure 31, and a corresponding number of lower vertical members 34. Both the upper and lower vertical members 32, 34 extend in a direction that is generally parallel to a longitudinal axis 40 of the support structure 31, and help to define the generally cylindrical shape of the support structure 31. Upper vertical members 32 extend generally toward the outflow end 24 of the valve structure 12, and the lower vertical members 34 extend in a direction that is generally opposite to the direction of the upper vertical members 32, which is toward the inflow end 22 of the valve structure 12.

Each of these upper and lower vertical members 32, 34 are preferably spaced from adjacent upper and lower vertical members 32, 34, respectively, by a distance that is similar or identical to the distance that the stent posts (e.g., stent posts 16) are spaced from each other in a corresponding implanted heart valve (e.g., heart valve 10). Thus, both the number of upper vertical members 32 and the number of lower vertical members 34 are typically the same as the number of stent posts. However, it is possible that the number of upper and lower vertical members 32, 34 are not the same as each other and/or not the same as the number of stent posts.

The upper vertical members 32 are designed to have a height that allows them to have a desired amount of contact with a corresponding stent post. The upper vertical members 32 may extend at least slightly beyond the tops of the stent posts, or may be at least slightly shorter than the stent posts. The lower vertical members 34 may also have any length that allows them to have a desired amount of contact with their corresponding stent posts 16 and other portions of the stent structure 12 with which they come into contact. Again, the lower vertical members 34 may extend at least slightly below the bottom of the stent structure (i.e., stent ring 14 of FIG. 1), or may be at least slightly shorter so that they do not extend below any portion of the stent structure. The selection of the length of these upper and lower vertical members 32, 34 can vary widely, depending on the configuration of the valve structure and the amount of contact desired between the support structure 31 and the interior portion of the stent or valve structure. In any case, the height of upper and lower vertical members 32, 34 should be adequate to provide sufficient contact between the support structure 31 and the corresponding heart valve in which it is positioned to keep the stent 30 in place relative to the heart valve. In addition, the arrangement of upper and lower vertical members 32, 34 should provide sufficient structural integrity to the support structure 31 so that it is resistant to deformation or other changes that impact its effectiveness as a stent structure.

The upper and lower vertical members 32, 34 may be generally "U" or "V" shaped, as illustrated, with the distance between opposite "legs" or extending portions of the members being chosen to provide desired characteristics to the support structure 31. For example, in FIG. 1, the upper vertical members 32 are preferably narrow enough that they will not unintentionally engage with the top edge of corresponding stent posts 16, but are preferably wide enough that they provide adequate contact with the interior portion of the stent posts 16 to help keep the stent 30 in place. In other words, the distance between opposite legs of the "U" or "V" shaped structure is preferably not so large that the members 32 can latch onto the stent posts 16, but is preferably large enough to provide contact between the members 32 and some portion of the interior surface of the stent posts 16. This "U" or "V" shaped structure of these members 32, 34 is particularly adaptable to the configuration where the support structure 31 is essentially a continuous wire structure; however, if the support structure is configured in another manner (e.g., with separate components that are not wire-like), each of the members 32, 34 may essentially consist of a single, relatively solid extending structure, for example. These structures may be arranged and connected relative to each other in a similar configuration to that described relative to a wire structure.

As shown in FIG. 1, heart valve 10 includes three stent posts 16 that are spaced generally at an equal distance from each other around the perimeter of the valve 10 (i.e., approximately 120 degrees apart). These stent posts 16 will generally correspond with the commissures of leaflets of the valve (not shown). It is understood, however, that the stent posts 16 may instead be unevenly spaced from each other. In one example of such an embodiment, first and second stent posts 16 may be spaced from each other by approximately 120 degrees, second and third stent posts 16 may be spaced from each other by approximately 115 degrees, so that first and third stent posts 16 would be spaced from each other by approximately 125 degrees. Other arrangements that vary slightly or substantially from this arrangement may alternatively be used; particularly in cases where more or less than two stent posts 16 are used. One example of such an arrangement would be in the case of a two-leaflet valve (e.g., the mitral valve), which would only include two stent posts arranged at approximately 180 degrees from each other and a corresponding arrangement for its support structure 31.

Support structure 31 further includes multiple upper flange or petal portions 36, each of which is located generally between two adjacent upper vertical members 32, and multiple lower flange or petal portions 38, each of which is located generally between two adjacent lower vertical members 34. The upper and lower flange portions 36, 38 are provided for engagement with the stent or valve structure 12 on generally opposite edges (i.e., top and bottom edges) of the stent ring 14 when positioned within a heart valve 10. That is, the upper flange portions 36 will be positioned in the area between adjacent stent posts 16 on the outflow end 24 of the valve structure 12, and the lower flange portions 38 will be positioned generally below the upper flange portions 36, but on the opposite side of the valve structure 12 (i.e., along the bottom edge of the stent ring 14 on the inflow end 22 of the valve structure 12).

Orientation and positioning of the stents of the invention may be accomplished either by self-orientation of the stents (such as by interference between features of the stent and a previously implanted stent or valve structure) or by manual orientation of the stent, such as by manipulation of its delivery system, to align its features with anatomical or previous bioprosthetic features, such as can be accomplished using fluoroscopic visualization techniques, for example. For example, when aligning the stents of the invention with a previously implanted bioprosthetic valve, features of the stents can align with the stent rail and/or commissures of the valve. It is desirable that the stents be locked in place both rotationally and axially.

Referring again to FIG. 1, the length and shape of each of these upper and lower flange portions 36, 38 can be the same or different from each other within a single support structure 31, as desired. The upper and lower flange portions 36, 38 may be generally "U" or "V" shaped, as illustrated, although the distance between opposite "legs" or extending portions of the members will generally be larger than the distance between the legs of the upper and lower vertical members 32, 34 within the same stent 30, particularly when the stent 30 is in its expanded state. Each upper flange portion 36 includes a distal tip 44 and each lower flange member 38 includes a distal tip 46. The tips 44, 46 may have a tighter curvature than the rest of their respective flange portions 36, 38, if desired. The tips 44, 46 may also serve as interfaces or connecting portions with a corresponding delivery system, as will be explained in further detail below.

The lower flange portions 38 are configured to engage with the lower surface of a sewing ring 14 of a previously implanted prosthetic heart valve (e.g., heart valve 10) when the stent 30 is in its expanded condition. Alternatively, the lower flange portions 38 can be configured to engage other structure(s) of the previously implanted prosthetic heart valve. Referring to FIG. 1, in order to engage with a previously implanted heart valve, one exemplary embodiment of a lower flange portion 38 includes a wire structure that extends generally from a common area 42 on one upper vertical member 32 toward the tip 46 of the flange portion 38, then toward another common area 42 on an adjacent upper vertical member 32. The curvature or contours of each flange portion 38 can be designed so that it closely matches the shape of the stent or valve structure 12 in which it will be implanted, such as at its inflow end 22. That is, there is preferably minimal to no gap between the flange 38 and the interior surface of the valve structure 12.

Each of the tips 46 of the flange portions 38 are positioned approximately 120 degrees from each other around the periphery of the sewing ring 14, although they can be spaced differently from each other, depending on the locations of the stent posts of the heart valve. When the stent 30 is in an expanded condition, the lower flange portions 38 are preferably biased toward the sewing ring 14 to keep the flange portion 38 in place relative to the heart valve 10.

The upper flange portions 36 are configured to engage with the spaces between stent posts 16 of a previously implanted heart valve (e.g., heart valve 10) when the stent 30 is in its expanded condition. Alternatively, the upper flange portions 36 can be configured to engage other structure(s) of the previously implanted prosthetic heart valve. In order to engage with a previously implanted heart valve, one exemplary embodiment of an upper flange portion 36 includes a wire structure that extends generally from a common area on one upper vertical member 32 toward the tip 44 of the flange portion 36, then toward another common area on an adjacent vertical member 32. The curvature or contours of each flange portion 36 can be designed to closely match the shape of the stent or valve structure 12 in which it will be implanted. Each of the tips 44 of the flange portions 36 are positioned approximately 120 degrees from each other around the periphery of the sewing ring 14, although they can be spaced differently from each other, depending on the locations of the stent posts of the heart valve. In any case, the tip 44 of flange portion 36 will preferably fit between adjacent stent posts 16 in order to help physically dock or connect the stent 30 to the previously implanted heart valve 10. When the stent 30 is in an expanded condition, the upper flange portions 36 are preferably biased toward the sewing ring 14 (and preferably toward a corresponding lower flange portion 38) to keep each flange portion 36 in place relative to the heart valve 10.

The support structure 31 of the stent 30 is, in one embodiment, a wire stent capable of transitioning from a collapsed state to an expanded state, where a number of individual wires comprising the support structure 31 are formed of a metal or other material. These wires are arranged in such a way that a support structure 31 is provided that allows for folding or compressing to a contracted state in which its internal diameter is at least somewhat smaller than its internal diameter in an expanded state. In its contracted state, such a support structure 31 with attached valves can be mounted relative to a delivery device, and the support structure 31 is configured so that it can be changed to its expanded state when desired. The delivery systems of the invention used for such replacement heart valve can optionally be provided with degrees of rotational and axial orientation capabilities in order to properly position the new heart valve within the previously implanted heart valve.

The wires of the support structure 31 can alternatively be formed from a shape memory material such as a nickel titanium alloy (e.g., Nitinol). With this configuration, the support structure 31 is self-expandable from a contracted state to an expanded state, such as by the application of heat, energy, and the like, or by the removal of external forces (e.g., compressive forces), such as external forces provided by the delivery system. In addition, the support structure 31 of this embodiment may be laser cut from a single piece of material or may be assembled from a number of different components. For these types of stent structures, one example of a delivery system that can be used includes a catheter with a retractable sheath that covers a compressed stent (thereby providing external compressive forces on the stent) until it is to be deployed, at which point the sheath can be retracted to allow the stent to expand.

The support structure 31 can include features not specifically described or shown instead of, or in addition to, the various coupling structures and methods described herein. For example, the support structure 31 can have a non-expandable design, but can instead be sized and shaped to nest within a previously implanted heart valve (not shown) in a manner that presses features of the previously implanted heart valve (e.g., leaflets) outwardly relative to the native conduit.

The height and diameter of the stent 30 in its expanded state is preferably chosen and/or designed for use with a previously implanted prosthetic heart valve having a particular size and shape. Thus, the stent 30 can assume a variety of different longitudinal heights and/or diameters. In one embodiment, for example, the support structure 31 has a height in its expanded state that is slightly greater than a height of the previously implanted prosthetic heart valve, and/or has a free-standing outer diameter that is greater than an inner diameter of the previously implanted prosthetic heart valve. With this embodiment, upon transitioning toward the expanded state, the support structure 31 (including the vertical members 32, 34) presses against an inner diameter of the previously implanted prosthetic heart valve. The overall shape of the support structure 31 is cylindrical in many cases; however, other shapes are also contemplated, such as elliptical, oval, or the like. For example, portions of the support structure 31 can define an enlarged diameter as compared to other portions. Further, depending upon the previously implanted heart valve being functionally replaced, the support structure 31 can be less uniform along a height thereof.

Figures 16, 17:
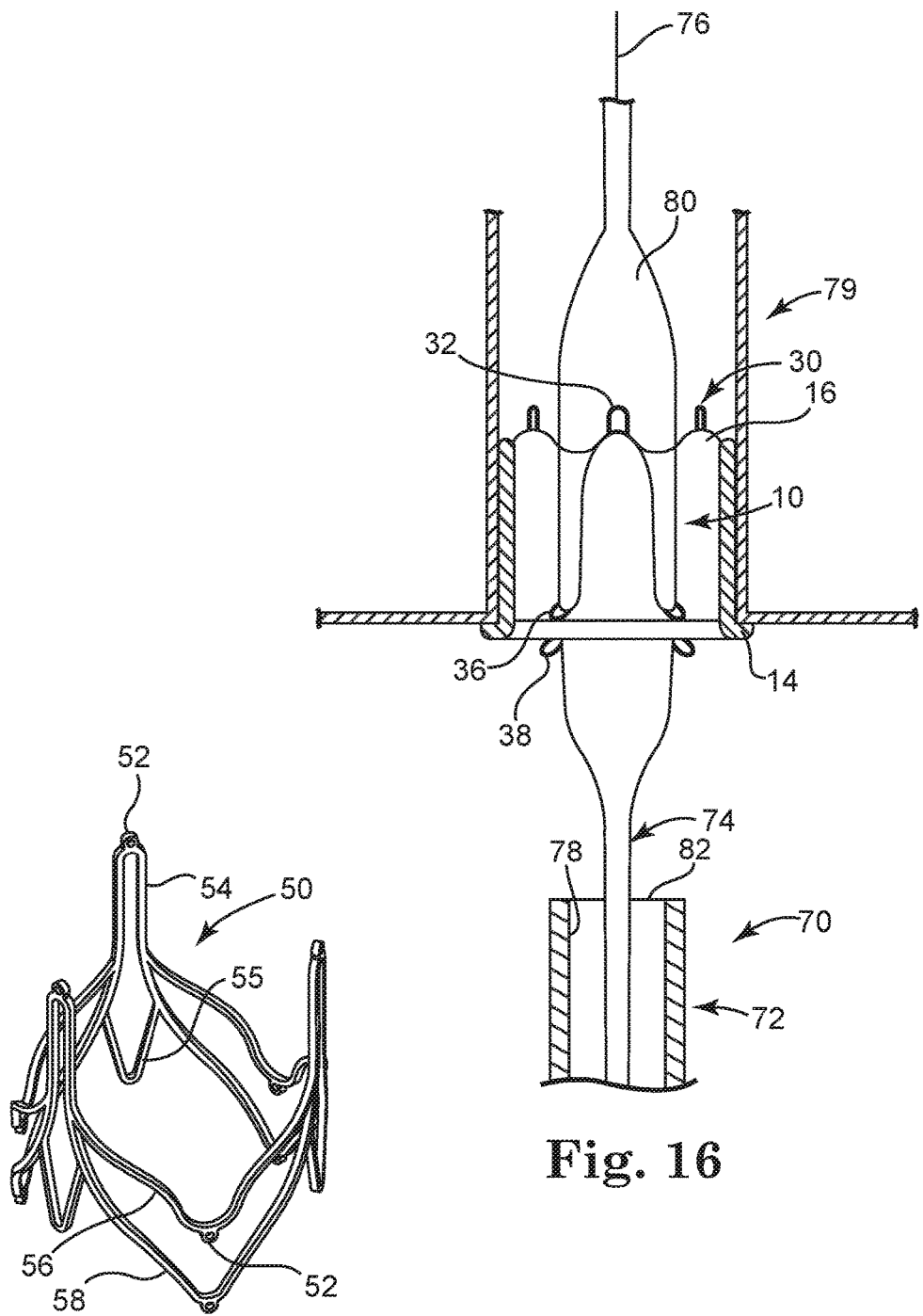
FIG. 16 is a partial-cross sectional side view of one embodiment of a delivery system for implanting a balloon-expandable stent.
FIG. 17 is a perspective view of another stent embodiment as it can be used as a component of a replacement heart valve.

One method of delivering a stent (e.g., stent 30) to the location of a previously implanted heart valve (e.g., heart valve 10) is performed percutaneously, as represented in simplified form in FIG. 16. In general terms for this exemplary delivery system, a transcatheter assembly 70 is provided, including a delivery catheter 72, a balloon catheter 74, and a guide wire 76. The delivery catheter 72 is of a type known in the art, and defines a lumen 78 within which the balloon catheter 74 is received. The balloon catheter 74, in turn, defines a lumen (not shown) within which the guide wire 76 is slidably disposed. Further, the balloon catheter 74 includes a balloon 80 that is fluidly connected to an inflation source (not shown). It is noted that if the stent being implanted is a self-expanding type of stent, the balloon would not be needed and a sheath or other restraining means would instead be used for maintaining the stent in its compressed state until deployment of the stent. In any case, in this embodiment, the transcatheter assembly 70 is appropriately sized for a desired percutaneous approach to the prosthetic heart valve 10 that was previously implanted in a native heart valve 79. For example, the transcatheter assembly 70 can be sized for delivery to the heart valve 10 via an opening at a carotid artery, a jugular vein, a sub-clavian vein, femoral artery or vein, or the like. Essentially, any percutaneous intercostals penetration can be made to facilitate use of the transcatheter assembly 70.

Prior to delivery, the stent 30 is mounted over the balloon 80 in a contracted state to be as small as possible without causing permanent deformation of the stent structure. As compared to the expanded state, the support structure 31 is compressed onto itself and the balloon 80, thus defining a decreased inner diameter as compared to an inner diameter in the expanded state. Further, the vertical members 32, 34 and flange portions 36, 38 are compressed toward the longitudinal axis 40 when in the contracted state. While this description is related to the delivery of a balloon-expandable stent, the same basic procedures can also be applicable to a self-expanding stent, where the delivery system would not include a balloon, but would preferably include a sheath or some other type of configuration for maintaining the stent in its compressed condition until its deployment.

With the stent 30 mounted to the balloon 80, the transcatheter assembly 70 is delivered through a percutaneous opening (not shown) in the patient via the delivery catheter 72. The previously implanted heart valve 10 is located by inserting the guide wire 76 into the patient, which guide wire 76 extends from a distal end 82 of the delivery catheter 72, with the balloon catheter 74 otherwise retracted within the delivery catheter 72. Once the previously implanted heart valve 10 has been located, the balloon catheter 74 is advanced distally from the delivery catheter 72 along the guide wire 76, with the balloon 80 and stent 30 positioned relative to the previously implanted heart valve 10. More particularly, the balloon 80 and stent 30 are positioned within the internal region of the previously implanted prosthetic heart valve 10, with the lower flange portions 38 positioned adjacent the sewing ring 14 of the heart valve 10, and the upper flange portions 36 are positioned adjacent the outflow end 24 of the previously implanted prosthetic heart valve 10.

With a stent in its contracted state, its support structure can readily move within the internal area of the previously implanted prosthetic heart valve, and any vertical members and flange portions, which are otherwise retracted or compressed, do not unintentionally contact or engage portions of the previously implanted prosthetic heart valve. In one embodiment, the stent includes a radiopaque, echogenic, or Mill visible material to facilitate visual confirmation of proper placement of the stent relative to the previously implanted prosthetic heart valve. Alternatively, other known surgical visual aids can be incorporated into the stent.

The techniques described above relative to placement of the stent within the heart can be used both to monitor and correct the placement of the stent in a longitudinal direction relative to the length of the anatomical structure in which it is positioned and also to monitor and correct the orientation of the stent relative to the stent posts 16 of the previously implanted heart valve. In particular, it is desirable for the stent to be positioned so that each of its upper flange portions are between two adjacent stent posts when they are expanded outwardly.

Once the stent is properly positioned, the balloon catheter 74 is operated to inflate the balloon 80, thus transitioning the stent to the expanded state, such as is shown in FIG. 1 relative to stent 30. Alternatively, if the support structure is formed of a shape memory material, the stent can be allowed to self-expand to the expanded state of FIG. 1. Thus, a self-expanding stent structure can be percutaneously delivered by an appropriate catheter device other than a balloon catheter, as will be described in further detail below. In either case, the support structure expands within the internal region 20 of the previously implanted heart valve 10, radially pressing against the valve structure 12. Because the previously implanted prosthetic heart valve 10 would have included leaflets (not shown), radial expansion of the stent would press against these leaflets, thereby lodging them against the valve structure 12.

FIG. 17 illustrates an embodiment of another exemplary stent 50 that includes a number of eyelets or apertures 52 that can be used for maintaining the various components of stent 50 in a compressed state when desired. These eyelets 52 can be particularly useful in the case where the stent 50 is a self-expanding stent, since this type of structure needs external forces to keep it in its compressed state. In particular, an eyelet 52 may be located at the end of at least one of the multiple upper vertical members 54 and/or one or more of the upper and lower flange portions 56, 58 and the lower vertical members 55. Each eyelet 52 is preferably sized for accepting an elongated thread-like material, such as suture material or a thin wire, and/or sized for engagement with a hook or other engagement feature of a delivery device. If a thread-like material is used, it can be threaded through at least one of the eyelets 52 in such a way that when the material is pulled tight, the eyelets 52 are pulled toward the central axis of the stent 50. If a wire-like material is used, it may be configured as a metal snare or other configuration that pulls the eyelets 52 toward the central axis of the stent 50. If a delivery device having such engagement features is used, it may be configured in such a way that the engagement features can be moved toward and away from the central axis of the stent, as desired for insertion and deployment of the stent.

Other arrangements of pulling the various portions of a stent toward a central stent axis are also contemplated, which preferably are relatively easy to operate for compression and release of the stent structures. In any case, once the stent structure is compressed to its desired configuration, the feature used to pull the stent into its compressed configuration is capable of being secured or fastened in some way to keep the stent from unintentionally expanding. This same feature can have its operation reversed to allow the various structures of the stent to move toward their expanded state.

FIGS. 18-21 illustrate one exemplary system of delivering a stent of the type illustrated in FIG. 17, for example, into a heart valve 10, which would have previously been implanted in a patient. One feature provided by the delivery system of this embodiment is that it allows a self-expanding stent to be retrieved after its initial deployment if it is not positioned correctly in the heart. The stent then could be redeployed into the proper position, using the same or a different delivery system. With particular reference to the Figures, a distal portion of a delivery system 90 is illustrated, which includes a tip portion 92 and a sheath 94. The system further includes a plurality of hooks or engagement features 96 that can engage with eyelets 52 of stent 50, for example. While this delivery system 90 can generally be used for more procedures than the described implantation procedure, the procedure illustrated relative to FIGS. 18-21 is particularly directed to percutaneous delivery of a stent to a previously implanted aortic heart valve via a retrograde approach. For purposes of this description of an implantation method, the exemplary stent 50 of FIG. 17 is used in the implantation description; however, a number of different stent embodiments may utilize these same procedures, such as other stent embodiments described herein.

Figures 18, 19:
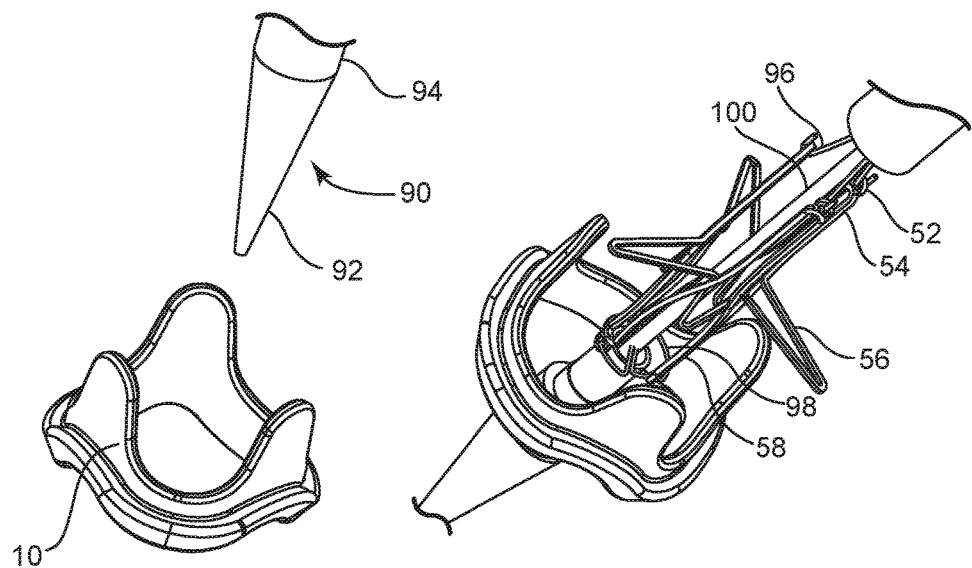
FIGS. 18-21 are sequential perspective views of the implantation of a self-expanding stent in a prosthetic heart valve, utilizing a retrograde approach of implantation.

As illustrated in FIG. 18, delivery system 90 is being advanced toward heart valve 10 as such a heart valve would have been previously implanted in a patient. The compressed replacement valve (not shown) is encompassed within sheath 94 for insertion into the patient so that there is no contact between the replacement valve and any portion of the patient's internal anatomy during the insertion process.

FIG. 19 illustrates delivery system 90 as it has been further advanced into heart valve 10, and wherein the sheath 94 has been partially retracted away from the tip 92 to expose a portion of the stent 50 that was previously compressed therein. Because the upper flange portions 56 are no longer constrained by the sheath 94, these portions 56 are able to move away from a central member 100 of the delivery system 90 as the sheath 94 is retracted. Further, eyelets 52 that extend from the ends of upper vertical members 54 are each engaged with a hook 96 of the delivery system 90. These hooks 96 can be attached to a mechanism within the interior portion of the sheath 94, for example, or may be attached to some other structure that extends through the sheath 94. In either case, hooks 96 can maintain the upper vertical members 54 in their compressed state until they are disengaged from the hooks 96. That is, the delivery system can control the diameter of the stent inflow structures, the stent outflow structures, or both the stent inflow and outflow structures independently or together. As is also illustrated in FIG. 19, the lower flange portions 58 are held in their compressed state with a snare 98 that engages with eyelets 52 that extend from each of the flange portions 58. Snare 98 is shown as a single, shaped piece of elongated material; however, the lower flange portions 58 may instead be held in their compressed state via an alternative structure or system, such as by a suture, or by a moveable sleeve attached to the delivery system, for example.

Figures 20, 21:
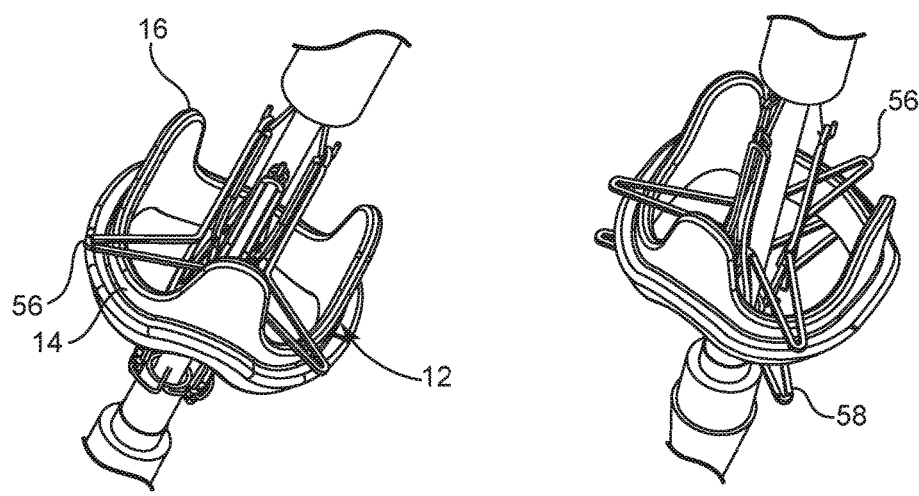

As shown in FIG. 20, the delivery system 90 is further advanced into valve 10 until the upper flange portions 56, which are extending radially away from the central member 100 of the delivery system 90, become engaged with the valve structure 12 of the heart valve 10. In particular, each of the upper flange portions 56 are preferably positioned to be in contact with the surface of the stent ring 14 between two adjacent stent posts 16. In order to verify that the flange portions 56 are properly positioned relative to the valve structure 12 (e.g., flange portions 56 are not resting on the top of the stent posts 16), the entire delivery system 90 can be rotated slightly in either direction while pressing downwardly toward the valve structure 12. The system 90 can also be advanced axially to the desired position. In this way, the flange portions 56 can be moved into the area between adjacent stent posts 16 if they are not already in this position.

Once the delivery system 90 and its stent 50 are properly oriented, the snare 98, sheath, or other structure holding the lower flange portions 58 in their compressed state is released or retracted, thereby allowing the lower flange portions 58 to deploy or radially extend, as illustrated in FIG. 21. The lower flange portions 58 can then contact the surface of the stent ring 14 that is opposite the surface that is contacted by the upper flange portions 56. The hooks 96 can then be disengaged from the eyelets 52 of stent 50, such as by further advancing the delivery system 90 into the opening of the valve 10, or by activating a mechanism associated with the hooks 96 that can move the hooks 96 relative to the eyelets 52 until they become disengaged from the eyelets 52. It is noted that the stent is retrievable at any point prior to the hooks 96 being disengaged from the stent 50 with use of the hooks 96 and/or the sheath 94. The upper and lower vertical members 54, 55 are then free to expand radially until they contact the inner surface of the stent or valve structure 12. The upper and lower vertical members 54, 55 preferably are configured so that they will press against the inner surface of the valve structure 12 with sufficient force to provide further anchoring of the stent 50 within the previously implanted heart valve 10.

After the stent 50 is implanted and its various portions are deployed or released from a compressed state to an expanded state, the delivery system 90 can be removed from the patient. The stent 50 will then be in its deployed or expanded state, as is generally illustrated in FIG. 17, or in a similar manner to that illustrated in FIG. 1 relative to a stent 30.

Figure 2:
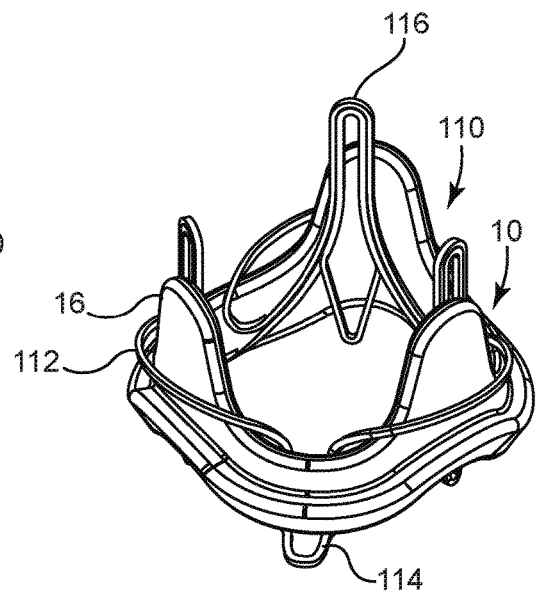
FIG. 2 is a perspective view of a prosthetic heart valve with another exemplary embodiment of a stent of a replacement prosthetic heart valve positioned therein.

FIG. 2 illustrates another exemplary embodiment of a stent 110 that has a similar structure to the stent 30 of FIG. 1, but further includes at least one stent post engaging structure 112. Relative to the specific embodiment of the stent 110 that is illustrated, this structure also does not include upper flange portions (such as upper flange portions 36 of stent 30), since such portions could be redundant and/or interfere with the specific structure of the structures 112 shown. However, it is contemplated that upper flange portions could also be provided with this embodiment, if they are configured to not interfere with any stent post engagement structures 112. Further, in the embodiment shown in this figure, three structures 112 are provided to correspond with a like number of stent posts 16 of heart valve 10; however it is contemplated that the stent 110 includes less than three structures 112, even if three stent posts are provided. If less than three structures 112 are provided, it may be desirable to additionally provide at least one upper flange portion to engage with the heart valve 10.

Each stent post engaging structure 112 is configured to partially surround a portion of a stent post 16, thereby providing another way of anchoring the stent 110 in place. These structures 112 can cooperate with one or more lower flange portions 114 to provide anchoring on both the inflow and outflow ends of the previously implanted heart valve 10. The structures 112 can be individual structures that are each secured to upper vertical members 116, or may be formed as a single structure having multiple loops that are secured to the structure of the stent 110. Alternatively, these structures 112 can be integrally formed with the structure of the stent 110. Stent 110 can be a self-expanding stent or may be a balloon-expandable stent structure.

Figure 3:
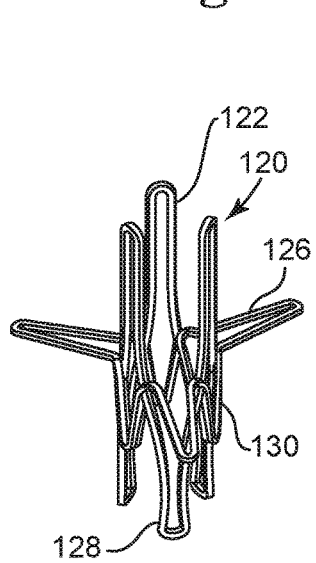
FIG. 3 is a perspective view of another exemplary embodiment of a stent of a replacement heart valve, with the stent in a partially compressed state.
Figure 4:
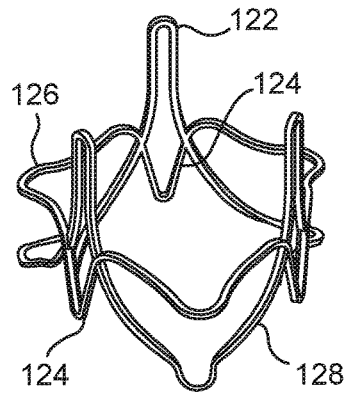
FIG. 4 is a perspective view of the stent of FIG. 3 in its expanded state.
Figure 5:
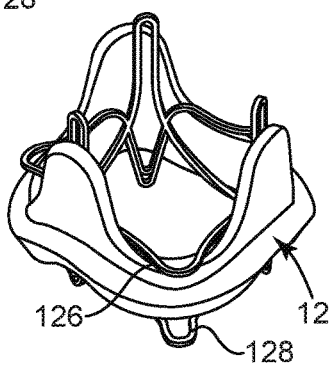
FIG. 5 is a perspective view of the stent of FIGS. 3 and 4 as positioned relative to a prosthetic heart valve.

FIGS. 3-5 illustrate another exemplary embodiment of a stent 120 for use with a replacement prosthetic heart valve in accordance with the present invention. Stent 120 includes a number of strut or wire portions arranged relative to each other to provide secure coupling between the stent 120 and a previously-implanted prosthetic heart valve, such as heart valve 10. In addition, stent 120 provides a semi-rigid frame for the leaflets of the replacement heart valve, which will be attached to the interior portion of stent 120, as will be described in further detail below.

Stent 120 includes multiple upper vertical members 122 spaced apart from each other around the perimeter of the stent 120, and a corresponding number of lower vertical members 124. It is understood that the number of upper and lower vertical members can be different from each other, however. Both the upper and lower vertical members 122, 124 extend in a direction that is generally parallel to a longitudinal axis of the stent 120, thereby partially defining the generally cylindrical shape of the stent 120. Upper vertical members 122 extend generally toward the outflow end of the stent structure 12, and the lower vertical members 124 extend in a direction that is generally opposite to the direction of the upper vertical members 122, which is toward the inflow end of the stent structure 12. As with previously described embodiments, the number of upper and lower vertical members 122, 124 may or may not be the same as the number of stent posts of the stent structure 12. In addition, the length of upper and lower vertical members 122, 124 should be adequate to provide sufficient contact between the stent 120 and the stent structure 12 to help keep the stent 120 in place relative to the heart valve 10.

Stent 120 further includes upper and lower flange portions 126, 128, respectively. Flange portions 126, 128 are configured for positioning on opposite sides of a stent ring 14 of stent structure 12 when the stent is in its expanded state. Through the design and manufacturing of the stent 120, the flange portions 126, 128 can be biased toward each other when the stent is in its expanded condition in order to keep the stent 120 positioned properly relative to a stent structure 12.

Stent 120 includes components that can be made of materials that perform differently relative to deployment thereof. In particular, a portion of stent 120 can be expandable from its compressed state via the application of an internal radial force (e.g., inflation of a balloon), while another portion of stent 120 can be self-expandable such that the removal of radial compressive forces will allow that portion of stent 120 to expand without application of additional forces. Alternatively, different portions of the stent 120 can be made of different materials that are both self-expanding, or of different materials that are expandable via the application of an internal radial force. Although the components that comprise these two structures can vary, the stent 120 illustrated in FIGS. 3-5 includes a first component that is expandable through application of a radial force. This component may be made of a material such as stainless steel, for example. The first component includes the upper vertical members 122, lower vertical members 124, and lower flange portions 128, and can include a number of components attached to each other, or can be a single machined piece. This first component is illustrated in its compressed state in FIG. 3 and in its expanded state in FIGS. 4 and 5. The stent 120 further includes a second component that is self-expandable and may be made of a shape memory material such as a nickel titanium alloy (e.g., Nitinol). This second component includes the upper flange portions 126 and also a second lower vertical member 130 that can at least roughly duplicate the shape of the lower vertical member 124 of the first component.

When this stent 120 is implanted into a patient, a sheath or other mechanism of its delivery system will hold the self-expandable portions of the stent in a compressed state until such a mechanism is retracted or removed, thereby allowing the upper flange portions 126 to extend radially from the stent structure, as is illustrated in FIG. 3. These upper flange portions 126 are preferably positionable between adjacent stent posts of a previously implanted heart valve for proper orientation of the stent 120. Because the first component is not made from a self-expandable material, the first component of stent 120 will remain in its compressed state, as shown in FIG. 3, until it is expanded radially, such as via expansion by a balloon catheter that is positioned in its central opening. When fully inflated, such a balloon will be constrained by the stent structure 12 along a portion of its length, but portions of the balloon that are above and below the stent structure 12 can be allowed to expand further so that the balloon takes on an "hourglass" type of shape, thereby pressing the lower flange portions 128 outward and under the stent ring 14, as illustrated in FIG. 5. These lower flange portions 128 can thereby help to anchor the stent 120 relative to the heart valve in which it is positioned. Thus, FIG. 5 illustrates the stent 120 in its expanded state, where the upper and lower flange portions 126, 128 are positioned on opposite sides of stent ring 14, and where the vertical members 122, 124, 130 are positioned adjacent to the internal portion of stent structure 12.

Figure 6:
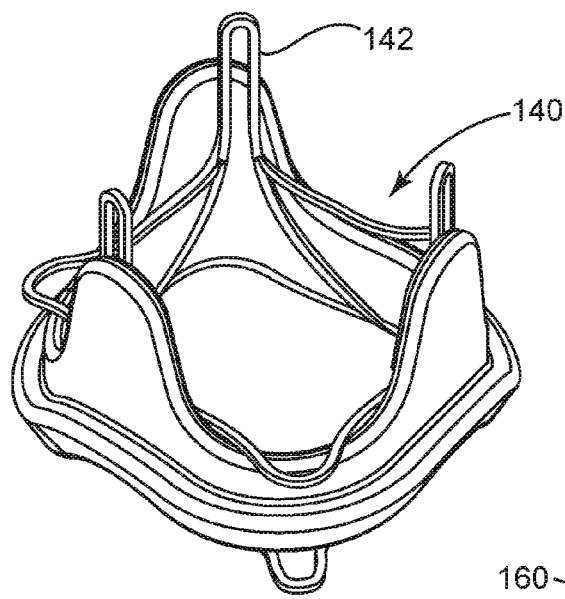
FIG. 6 is a perspective view of another exemplary embodiment of a stent of a replacement valve positioned within a prosthetic heart valve.

FIG. 6 illustrates another exemplary embodiment of a stent 140 for use as a replacement prosthetic heart valve in accordance with the invention. This stent 140 includes similar structures to those of the stent 30 of FIG. 1; however, stent 140 does not include lower vertical members that correspond to and extend in the opposite direction from upper vertical members 142. Otherwise, stent 140 can include any of the features described herein. Stent 140 can be self-expanding or expandable with application of a radial force, and pericardial tissue or other materials may be attached to its structure to provide a prosthetic heart valve.

Figure 7:
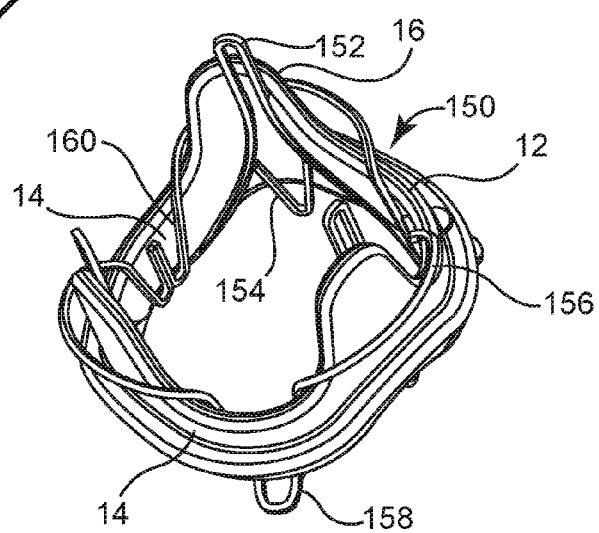
FIG. 7 is a perspective view of another exemplary embodiment of a stent of a replacement valve positioned within a prosthetic heart valve.

FIG. 7 illustrates another exemplary embodiment of a stent 150 for use as a replacement prosthetic heart valve in accordance with the present invention. Stent 150 includes similar structures to the stent 110 of FIG. 2, including upper vertical members 152 and corresponding lower vertical members 154, stent post engagement structures 156, and lower flange members 158. In an embodiment where the number of stent post engagement structures 156 is optionally less than the number of corresponding stent posts of the previously implanted heart valve, upper flange members may be included on stent 150, if desired. Alternatively, upper flange members may be included on stent 150 in a configuration that does not interfere with the structures 156.

Stent 150 further includes "W" shaped structures 160 positioned along the stent ring 14 between adjacent stent posts 16 in the interior area of the stent structure 12. Each structure 160 is positioned generally between adjacent lower flange members 158 and provides additional contact surfaces between the stent 150 and the interior portion of the stent structure 12. In addition, any or all of the structures 160 can be used to hold a leaflet of the failed bioprosthesis against the stent ring of the failed bioprosthesis (such as stent ring 14) so that the leaflets of the failed bioprosthesis do not interfere with the valve leaflets of the newly implanted valved stent. That is, it may be desirable to hold the leaflets of the failed bioprosthesis toward the stent ring in order to minimize the potential for formation of thrombus between the failed leaflets and the new leaflets. In addition, holding the leaflets against the stent ring can prevent abrasion and/or tearing of the new leaflets that can occur during repeated contact with the old leaflets. The structures 160 may take a "W" type shape, as shown, or may instead have a different shape, such as one or more "U" or "V" shapes, a series of extensions, a sinusoidal shape, or any desired configuration that can hold leaflets against the stent ring of the failed bioprosthesis, when desired.

The stent 150 may comprise any desired number of components that are connected or attached to each other; however, the exemplary embodiment of stent 150 illustrated in FIG. 7 provides an embodiment with two separate structures attached or arranged relative to each other. That is, a first component is a formed structure that includes the stent post engagement structures 156 and the "W" shaped structures 160, while a second component is a formed structure that includes the upper and lower vertical members 152, 154 and the lower flange members 158.

Figure 8:
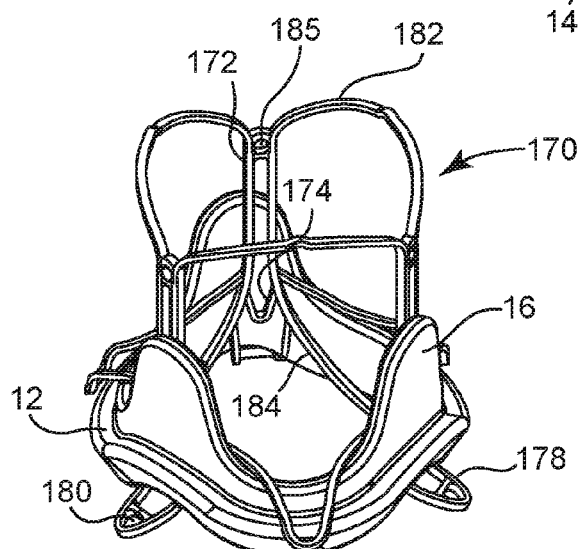
FIG. 8 is a perspective view of another exemplary embodiment of a stent of a replacement valve positioned within a prosthetic heart valve.

FIG. 8 illustrates another exemplary embodiment of a stent 170 for use as a prosthetic heart valve in accordance with the present invention. Stent 170 generally includes upper vertical members 172 and corresponding lower vertical members 174, upper flange members 176, lower flange members 178, and upper connecting members 182. In this embodiment, the upper flange members 176 are offset relative to lower flange members 178 such that each of the upper flange members 176 is positioned generally between adjacent stent posts 16 of stent structure 12, and each of the lower flange members 178 is generally aligned with the stent posts 16. Upper connecting members 182 extend between adjacent upper vertical members 172 and are provided for tying together the upper vertical members 172 to carry the valve hydrodynamic closing loads, which can thereby reduce various stresses in the stent. The upper connecting members 182 can also provide interface points for connection of the stent 170 with the delivery system used for the implantation process. Stent 170 further includes optional lower connecting members 184 that extend between adjacent lower vertical members 174. Lower connecting members 184 are provided for attachment of the material that makes up the leaflets of the replacement heart valve. That is, pericardial or another valve material may be sewn or otherwise attached to the lower connecting members 184 and may further be sewn or otherwise attached to the upper vertical members 172.

The upper connecting members 182 are shown as a single curved member; however, the connecting members can have any desired structure or configuration that provides the desired support for the upper vertical members 172. Further, the connecting members 182 may be made of the same or a different material than the other portions of the stent.

One or more of the lower flange members 178 may further include an eyelet or aperture 180 for engagement with a structure of a delivery system for use during the implantation of the stent 170 (e.g., sutures or a hook structure that can pull the stent structure toward its central axis). One or more of the upper vertical members 172 may similarly include an eyelet or aperture 185 for use during the implantation of the stent 170 and/or for use as an anchor point for attachment of valve material to the stent 170.

Figure 9:
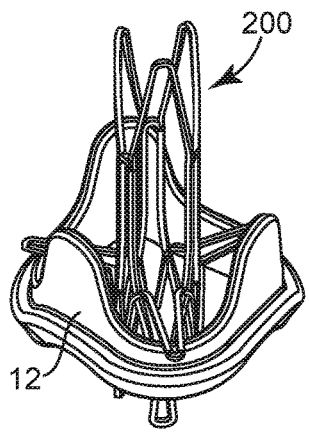
FIG. 9 is a perspective view of another exemplary embodiment of a stent of a replacement valve positioned within a prosthetic heart valve, with the stent in its partially compressed state.
Figure 10:
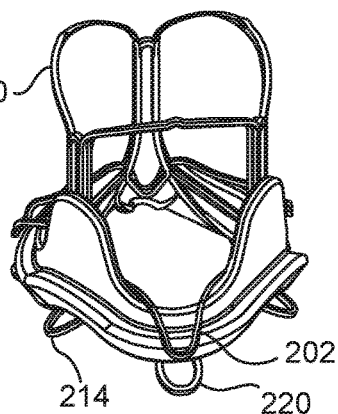
FIG. 10 is a perspective view of the stent of FIG. 9 positioned within a prosthetic heart valve, with the stent in its expanded state.
Figure 11:
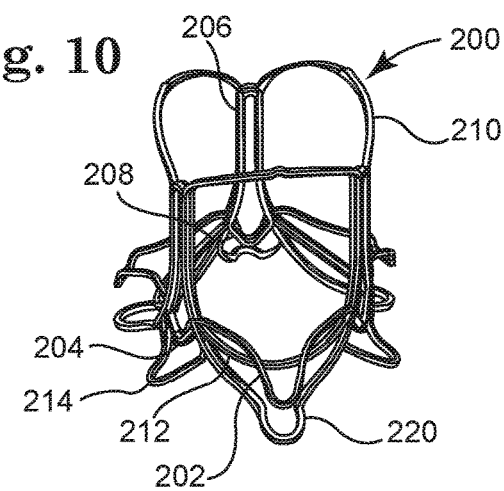
FIG. 11 is a perspective view of the stent of FIG. 10.

FIGS. 9-11 illustrate another exemplary embodiment of a stent 200 for use as a replacement prosthetic heart valve in accordance with the present invention. Stent 200 is similar to stent 120 of FIGS. 3-5 in that stent 200 also includes a portion that is made of a material that is expandable (e.g., stainless steel) with a device such as a balloon catheter, for example, and a portion that is made of a material that is self-expanding (e.g., Nitinol) when external forces are removed. In particular, a self-expanding portion of stent 200 may include upper flange portions 202 that can be generally positioned between adjacent stent posts 16 of a stent structure 12, and bracing portions 204 that can be generally aligned with stent posts 16 of a stent structure 12. The other portion (i.e., the portion that is not self-expanding) of the stent 200 may include any or all of the following structures: upper vertical members 206; lower vertical members 208; upper support structures 210 extending between adjacent upper vertical members 206; lower support structures 212 extending between adjacent lower vertical members 208, lower flange portions 220; and intermediate lower flange portions 214 located between adjacent lower flange portions 220. The lower flange portions 214 can provide additional anchoring force for the stent 200 against the stent structure 12 in the areas generally adjacent to the stent posts 16. The lower support structures 212 may be used for securing the valve structure to the stent 200, if desired.

Figure 12:
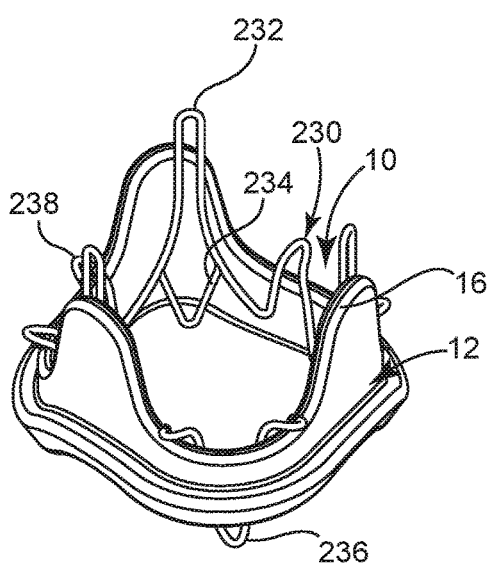
FIG. 12 is a perspective view of another exemplary embodiment of a stent of a replacement valve positioned within a prosthetic heart valve.

FIG. 12 illustrates another exemplary embodiment of a stent 230 for use as a prosthetic heart valve. Stent 230 includes multiple upper vertical members 232 and optional corresponding lower vertical members 234, and multiple lower flange members 236. The number of upper vertical members 232 and lower vertical members 234 preferably correspond to the number of stent posts of the previously implanted heart valve. In addition, the number of lower flange members 236 preferably corresponds to the number of stent posts 16 of the previously implanted heart valve 10 so that one lower flange member 236 can be positioned generally between two adjacent stent posts 16, but on the opposite side of the stent structure 12 from the stent posts 16. The stent 230 further includes multiple upper flange members 238, which are positionable in the space between every two adjacent stent posts 16, but on the same side of the stent structure 12 as the stent posts 16. In this embodiment, two upper flange members 238 are positioned in each of the spaces between two adjacent stent posts 16, which thereby provide additional anchoring points for the stent 230 within the stent structure 12. In addition, these flange members 238 can function similarly to the structures 160 described above relative to FIG. 7 in that one or more of the flange members 238 can help to hold the leaflets of the failed bioprosthesis generally against the stent ring of the bioprosthesis so that they do not interfere with the leaflets of the new valved stent. The stent 230 can be configured so that each of the upper flange members 238 of the pair of upper flange members are angled at least slightly toward their adjacent stent posts 16 so that they are facing in at least slightly opposite directions from each other.

Figure 13:
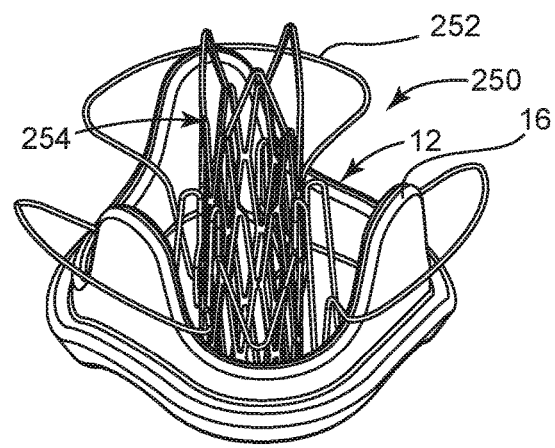
FIG. 13 is a perspective view of another exemplary embodiment of a stent of a replacement valve positioned within a prosthetic heart valve, with the stent in its partially compressed state.
Figure 14:
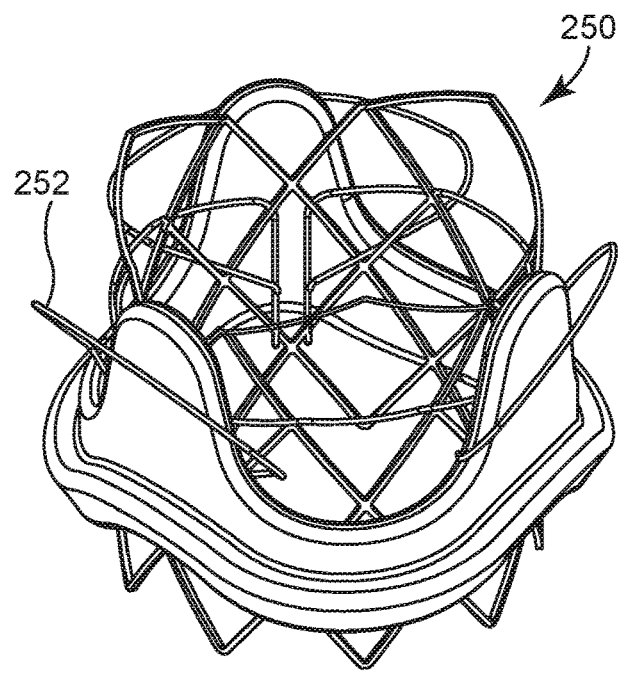
FIG. 14 is a perspective view of the stent of FIG. 13 in its expanded state as positioned within a prosthetic heart valve.

FIGS. 13 and 14 illustrate another exemplary embodiment of a stent 250 for use as a prosthetic heart valve. Stent 250 is similar to stent 120 of FIGS. 3-5 in that stent 250 also includes a portion that is made of an expandable material (e.g., stainless steel) with a balloon catheter, for example, and a portion that is made of a material that is self-expanding (e.g., Nitinol) when external forces are removed. In particular, a self-expanding portion of stent 250 may include multiple stent post engagement structures 252, which are shown in this embodiment as being part of a continuous unit or piece that is configured to include three stent post engagement structures 252. Each of the structures 252 is provided to engage with a stent post 16 of a stent structure 12. The other portion (i.e., the portion that is not self-expanding) of the stent 250 comprises a mesh-like stent structure 254 that includes a number of wire portions arranged as best illustrated in the expanded version of the stent 250 in FIG. 14. Although this embodiment does not illustrate particular flange portions that extend above or below the stent structure 12, it is contemplated that any of the anchoring structures discussed above may be incorporated into the stent 250 to provide additional anchoring mechanisms for the stent 250.

Figure 15:
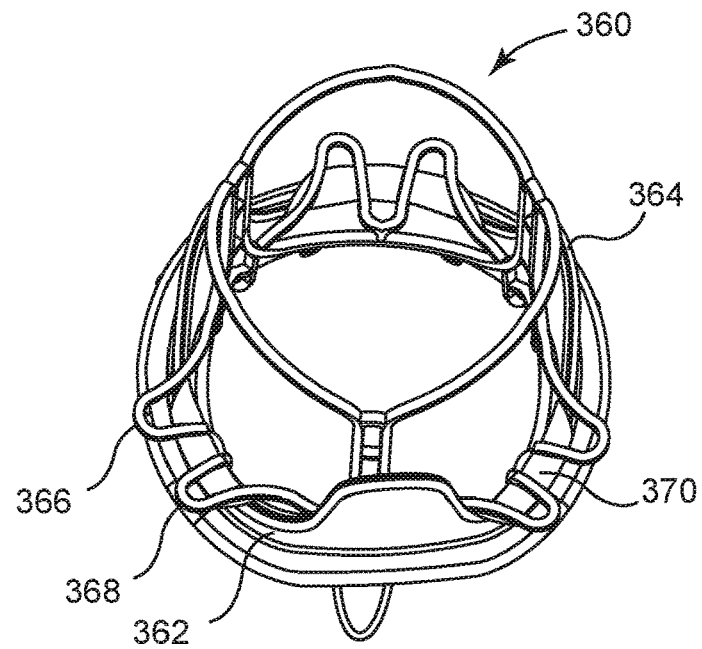
FIG. 15 is a perspective view of a prosthetic heart valve with a stent of a replacement prosthetic heart valve positioned therein and showing the leaflets of the original prosthetic heart valve.

FIG. 15 illustrates another stent 360 of the invention as it can be implanted within a previously implanted heart valve, such as a heart valve 362, and specifically illustrates an exemplary positioning of the leaflets 370 of the previously implanted heart valve 362. Stent 360 includes a split petal structure for its upper flange member that is positioned between stent posts 364, as shown with petals 366, 368. These petals 366, 368 provide two structures for holding the leaflets 370 of the heart valve 362 against the stent rail of that heart valve 362 so that the leaflets 370 do not interfere with the implantation and/or functioning of the newly implanted heart valve. The petals 366, 368 may have the same configuration as each other, as shown, or may instead be differently sized and/or shaped than each other. It is also contemplated that other structures may be used, such as a series of barbs or extending members, and it is further understood that more or less than two structures can be used for holding the leaflets 370 against the rail of the heart valve 362. The petal structures could also be used to hold native leaflets outward for the stented valve implanted in a native valve.

FIGS. 22-27 sequentially illustrate a delivery process for percutaneous delivery of a self-expanding type of stent into a prosthetic heart valve 320. In particular, FIG. 22 shows a distal tip 322 of a delivery system 324 as it is approaching heart valve 320, with a stent completely enclosed within an outer sheath 326 such that there is no contact between the stent (which will be a replacement valve when the leaflets are attached) and any portion of the patient's internal anatomy during the insertion process. The delivery system 324 is advanced further toward heart valve 320 until the distal tip 322 is adjacent to or at least partially inserted into the central area of the heart valve 320, or any desired location for deployment of the stent. The sheath 326 can then be partially retracted to release a portion of a stent 328, as shown in FIG. 23. As shown, stent 328 includes upper flange portions 330, upper vertical members 332, and upper connecting members 334 extending between adjacent upper vertical members 332. The upper connecting members 334 provide interface points for connection of the stent 328 with delivery system 324 used for the implantation process. In that regard, the upper connecting members 334 may optionally include one or more connection features that provide a more specific feature and/or portion for engagement with a portion of the delivery system, such as a groove 336 shown in FIG. 28, a loop, or some other engagement feature.

When the sheath 326 is partially retracted, as described above, the upper flange portions 330 are released from the interior of the sheath 326 and can expand or extend radially away from the central axis of the delivery system. In the illustrated embodiment, the upper flange portions 330 extend a sufficient distance from the delivery system 324 so that they can engage with the top surfaces (i.e., the outflow end) of the heart valve 320. More specifically, the upper flange portions 330 can preferably extend into the space between adjacent stent posts 338 of the heart valve 320. Thus, once the flange portions 330 are deployed, the delivery system 324 should be rotatable to orient the flange portions 330 in the spaces between adjacent stent posts 338. Such a positioning can be accomplished either using a wide variety of visualization techniques and/or through tactile feedback to the person doing the implantation.

Throughout the initial process of deploying the flange portions 330 in the implantation process, the upper connecting members 334 are engaged with a hook or other engagement device 340 of the delivery system 324. These devices 340 can be attached to a mechanism within the interior portion of the sheath 326, for example, or may be attached to some other structure that extends from the sheath or another portion of the delivery system. In this embodiment and as can best be seen in FIG. 26, an inner sheath member 342 includes an internal structure that supports multiple engagement devices 340. In this embodiment, engagement devices 340 are configured as loops, each of which has a free end 344. The structure of each of the devices 340 is designed and selected so that it can remain engaged with the upper connecting members 334 throughout the process of positioning the delivery system 324 and stent 328 in its desired position relative to the heart valve 320. Advantageously, after deployment of at least part of the stent 328, as shown in FIGS. 23-25, for example, the stent 328 can be retracted back into the delivery system 324, if desired or necessary, due to the continued engagement between the upper connecting members 334 and the engagement devices 340. That is, the delivery systems and stents of the invention advantageously provide opportunities for stent repositioning that are not typically available in the deployment of self-expanding stents.

At some point during the stent delivery, deployment, and repositioning process, the delivery system 324 can be further manipulated to release lower flange portions 346 from their compressed state within the delivery system 324. For example, the distal tip 322 can be further moved away from the sheath 326 to allow the lower flange portions 346 to expand or extend outwardly from the internal area of the distal tip 322. However, it is understood that the lower flange portions 346 may be confined and deployed in a wide variety of different ways, such as deployment methods that are discussed herein relative to various stent embodiments.

After the stent 328 is properly oriented and positioned relative to the previously implanted heart valve 320, the stent can be released completely from the delivery system 324 by increasing the force on the engagement devices 340 until the devices 340 disengage from the upper connecting members 334 of the stent 328. In this embodiment, the force can be increased to at least partially straighten the engagement devices 340 until their free ends 344 move past the connecting members 334, thereby disengaging the delivery system 324 from the stent 328, as illustrated in FIG. 27. FIG. 28 illustrates the stent 328 after the deployment process described above.

Figure 30:
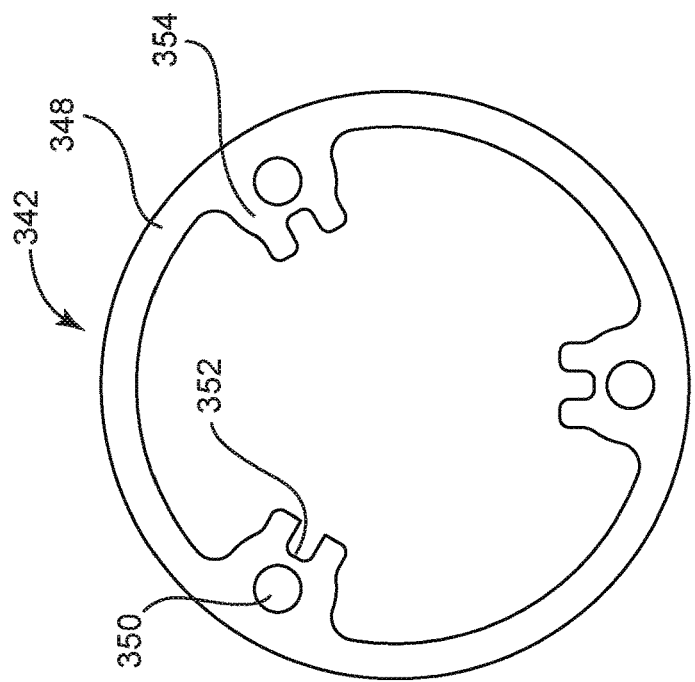
FIG. 30 is an end view of the sheath of the delivery system of FIG. 29.
Figure 29:
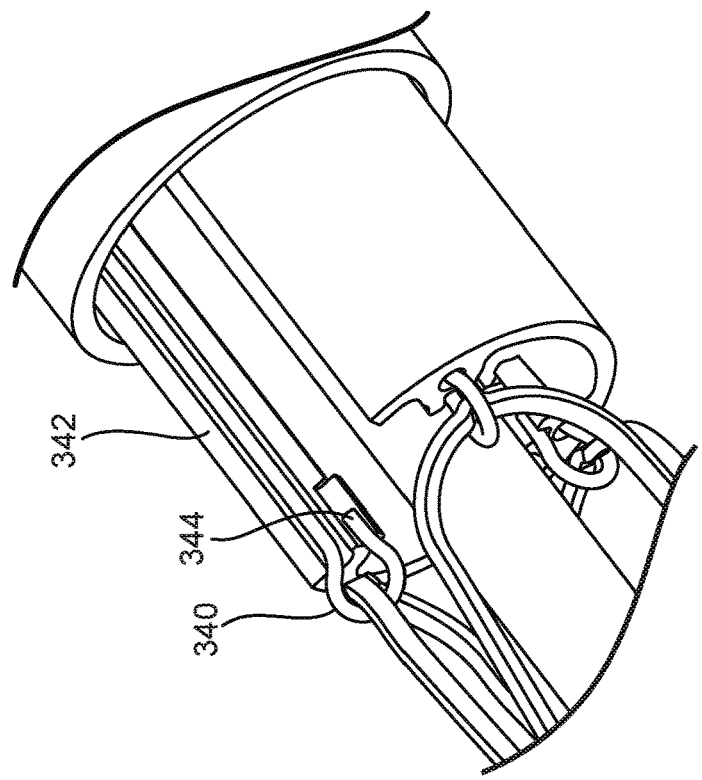
FIG. 29 is an enlarged perspective view of the delivery system and stent of FIG. 26, with a portion of the sheath removed for visibility of the stent engagement features.

FIGS. 29 and 30 illustrate further details of an embodiment of the inner sheath member 342 described above, along with the positional relationship between the inner sheath member 342 and engagement devices 340. In particular, inner sheath member 342 includes an outer shell 348 that is cylindrical or circular in shape, although it could have another shape, such as oval, elliptical, square, or another symmetrical or asymmetrical shape. Outer shell 348 includes multiple extensions 354 that protrude toward its internal area, where one extension is preferably provided for each of the engagement devices 340 of a particular delivery system. Each of the extensions 354 of this embodiment includes an aperture 350, which is sized to surround a portion of an engagement device 340, and an optional notch 352 positioned to maintain the free end 344 of an engagement device 340 in a particular orientation.

Figures 31, 32, 33:
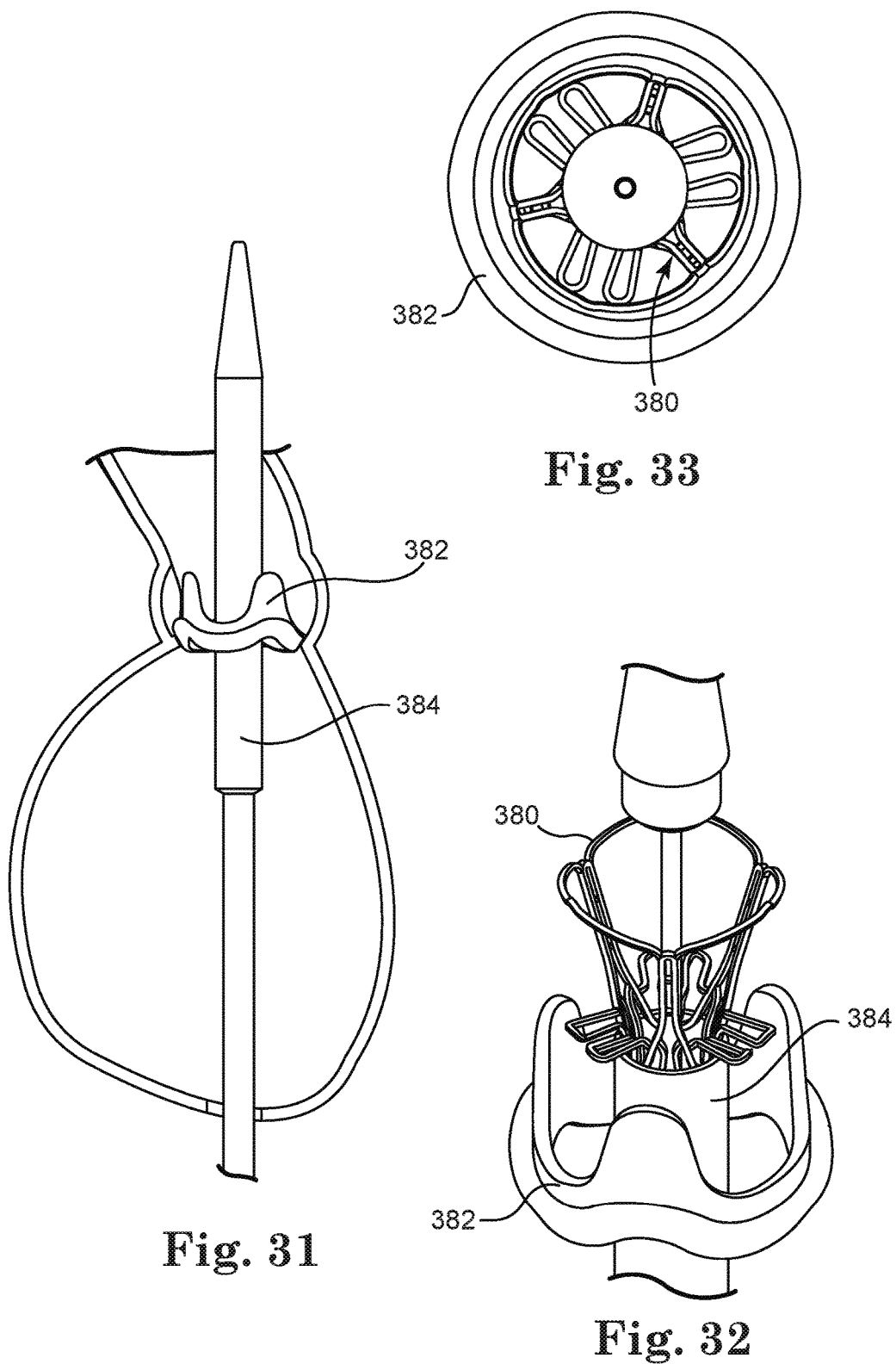
FIGS. 31-38 are a number of views of sequential steps for using a delivery device engaged with a stent of a replacement heart valve to position that valve in a prosthetic or native heart valve, including an initial step in FIG. 31, an intermediate deployment step in FIGS. 32-33 in which the outflow end of the stent expands, another deployment step in FIGS. 34-36 in which the inflow end of the stent expands, and a release of the stent from the delivery system in FIGS. 37-38.
Figure 34:
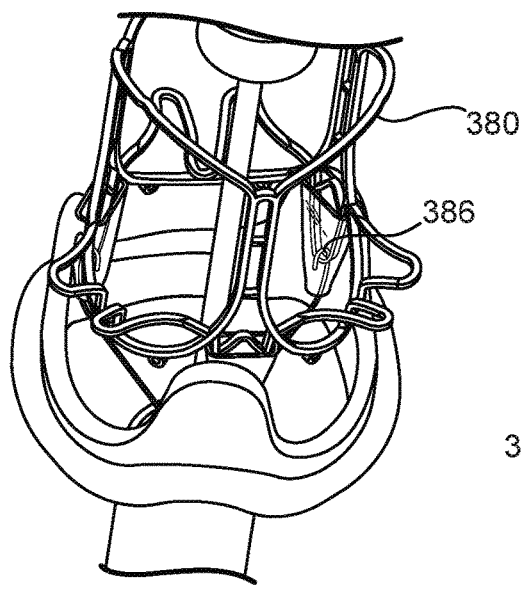
Figure 35:
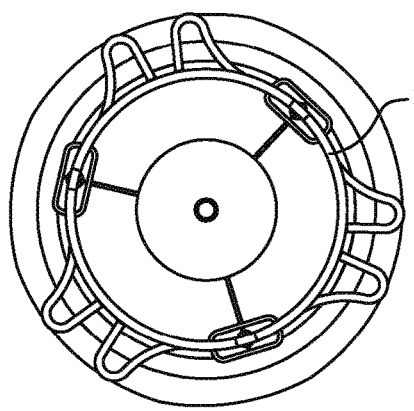

FIGS. 31-38 illustrate another exemplary delivery process for implanting a stent 380 into a previously implanted heart valve 382. FIG. 31 shows a basic first step of inserting a delivery device into the area of the failed heart valve or bioprosthesis 382, and then a sheath 384 is retracted (see FIGS. 32 and 33) to allow the outflow end of the stent 380 to expand or extend outwardly, since the stent 380 is a self-expanding stent structure. As described above, the stent 380 can remain engaged with the delivery device, even when the stent is partially deployed, in order to allow it to be pulled back into the sheath 384 if desired during certain aspects of the delivery and positioning process. In any case, the sheath 384 can then be further retracted to allow the inflow end of the stent 380 to further expand or extend outwardly, as illustrated in FIGS. 34 and 35. In this embodiment, the delivery system includes multiple engagement members in the form of hooks 386 that engage with the stent crown during positioning of the stent 380. Positioning of the stent 380 can include rotation of the delivery device to properly orient the stent. The hooks 386 can be remotely connected to a deployment or other activation mechanism that allows the hooks 386 to become disengaged from the stent 380, when desired.

Figure 36:
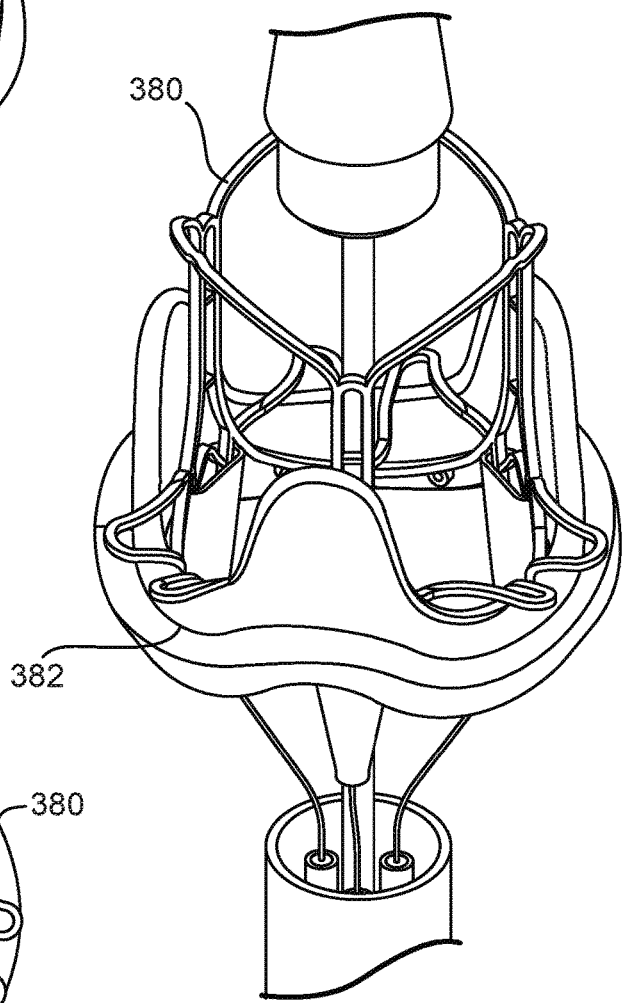
Figure 37:
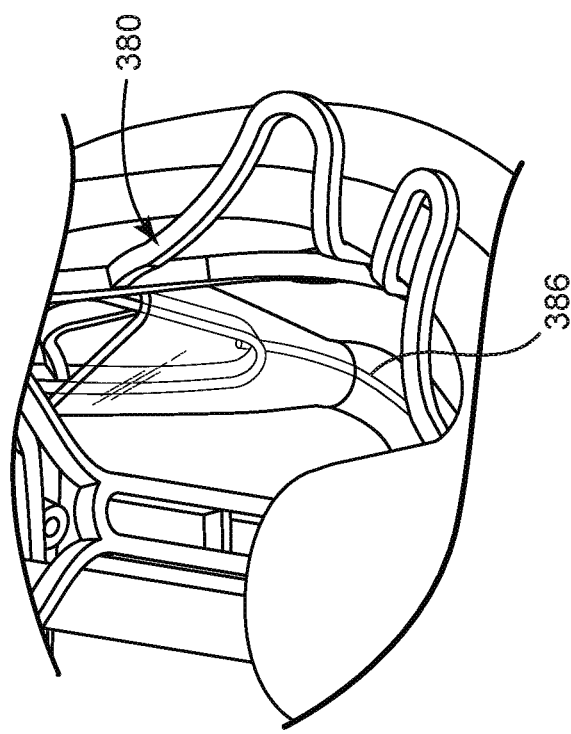

Next, the delivery device can be pulled back to seat the stent 380 against the rails of the heart valve 382, as shown in FIG. 36, while the hooks 386 remain engaged with the stent 380. When the final positioning of the stent 380 is complete, the wires that make up the hooks 386 can be pulled in such a way that the wires straighten sufficiently that they release from the stent 380, as shown in FIG. 37. Notably, the act of releasing the stent when it is fully expanded is advantageous in that it allows blood to flow through the valve during the delivery and implantation process. In addition, it allows the clinician to verify that the valve is properly positioned and seated with the valve in a fully expanded condition.

Figure 38:
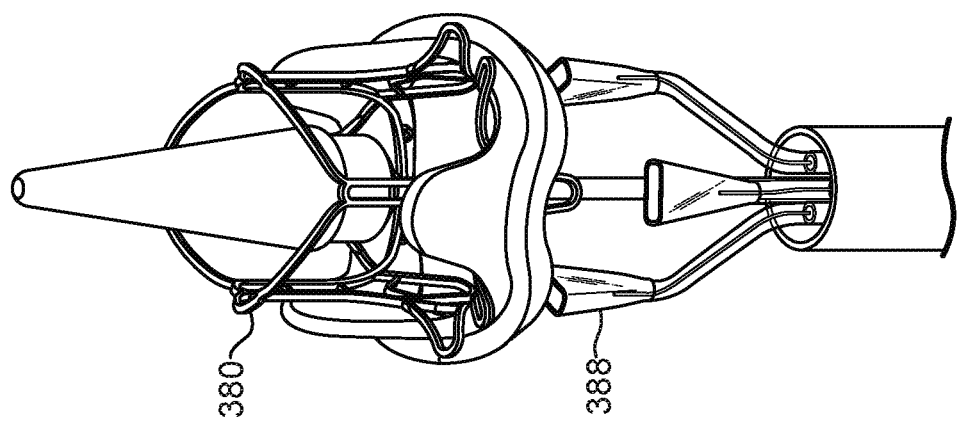

The delivery system can further include a tube or other covering structure 388 that at least partially surrounds the wires that comprise the hooks 386, especially when the delivery device is being manipulated within a patient. These structures 388 can be retracted before or after the wires they surround are disengaged from their respective stent structures, as shown in FIG. 38, thereby releasing the stent from the delivery system.

Figure 39:
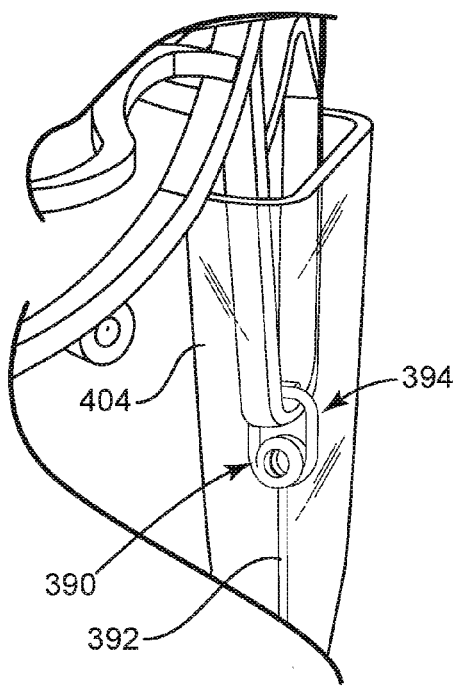
FIGS. 39-41 are perspective views of one embodiment of an engagement member of a delivery system as it is engaged with and released from a portion of a stent.
Figure 40:
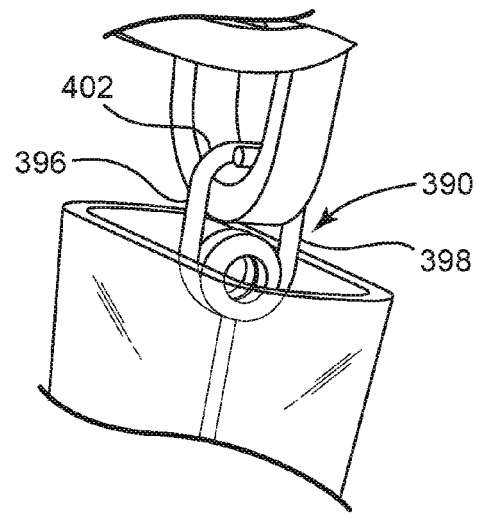
Figure 41:
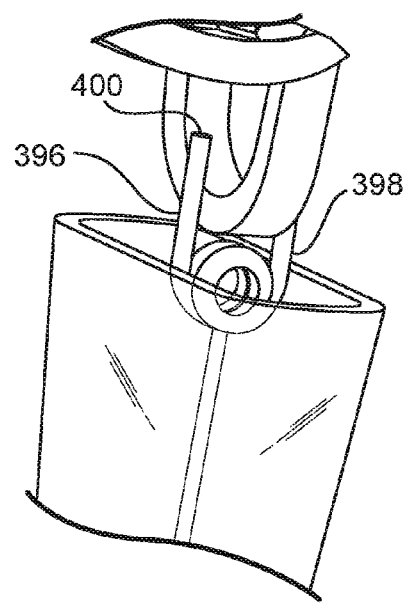

FIGS. 39-41 illustrate a portion of a delivery system that includes another embodiment of an engagement member 390 in the form of a clasp or spring-like structure that engages with a portion of a stent during delivery of the stent. In particular, the engagement member 390 includes a delivery wire 392 from which a clasping mechanism 394 extends. Clasping mechanism 394 includes two wire portions 396, 398 that are bent or curved near their distal ends 400, 402, respectively. In this embodiment, the wire portions 396, 398 are shaped so that their end portions extend over a wire of the stent with which the delivery system is engaged, and the wire portions 396, 398 optionally overlap each other at least slightly. As with other delivery systems described herein, the engagement member 390 (specifically, the clasping mechanism 394) will remain engaged with the stent until the stent is properly positioned and oriented. When the final positioning of the stent is complete, the delivery wire 392 can be pulled or otherwise manipulated in such a way that the wire portions 396, 398 straighten enough that they release from the stent, as shown in FIG. 41. It is understood that the wire portions 396, 398 can be shaped or formed differently than shown to provide more, less, or different functional engagement with the stent wires. For example, the wire portions 396, 398 may be formed in such a way that they rotate relative to each other to engage with and release the stent, rather than being deformed or straightened to release from the stent, as is generally illustrated in FIGS. 42 and 43.

The delivery system of FIGS. 39-41 can further include a tube or other covering structure 404 that at least partially surrounds the wire portions 396, 398 for at least part of the delivery process, such as when the delivery device is being manipulated within a patient. These structures 404 can be retracted before or after the wires they surround are disengaged from their respective stent structures.

FIGS. 44 and 45 illustrate a portion of a delivery system that includes another embodiment of an engagement member 410 in the form of a protrusion structure that engages with a portion of a stent during insertion and positioning of the stent. The protrusion can take many shapes or configurations, including the ball-like structure illustrated, although it is contemplated that the protrusion has any geometry, shape, and/or size that allows the protrusion to engage with an opening in the stent and retain the stent while covered. In particular, the engagement member 410 includes a delivery wire 412 from which a protrusion 414 extends. The delivery wire 412 is shaped so that the protrusion 414 can be positioned for engagement with a wire of the stent with which the delivery system is engaged, as shown in FIG. 44. As with other delivery systems described herein, the engagement member 410 (specifically, the protrusion 414) will remain engaged with the stent until the stent is properly positioned and oriented. When the final positioning of the stent is complete, the delivery wire 412 can be pulled or otherwise manipulated in such a way that the protrusion 414 disengages from the stent, as shown in FIG. 45. The delivery system of FIGS. 44 and 45 can further include a tube or other covering structure 416 that at least partially surrounds protrusion 414, such as when the delivery device is being manipulated within a patient. These structures 416 can be retracted before or after the wires they surround are disengaged from their respective stent structures, as desired.

In the portion of the delivery system embodiment shown in FIGS. 44 and 45, the engagement member 414 is described and shown as a relatively spherical member that engages with the wires of a stent. However, alternative engagement member configurations can be provided that function similarly to the illustrated engagement member, where these engagement members can extend from a delivery wire that is configured the same or differently from delivery wire 412, although the method of engagement with the stent wire(s) can be similar. For example, the engagement member may instead be configured more as a tab that can have a wide variety of shapes, such as triangular, rectangular, or elliptical, for a few examples. Any of these engagement members may further include an angled face that extends from a portion of the engagement member toward its associated delivery wire. Such an angled face can provide for easier engagement with and/or removal from the stent wire, for example, and can have a corresponding angle and size that provides the desired functional feature.

The tube or covering structures described above can additionally or alternatively serve the function of maintaining an engagement mechanism in its engaged position until it is desired to release the stent from the mechanism. For example, such a tube can surround a wire that is bent around a stent structure, then when the tube is retracted, the wire can spring or move to a different position to thereby release from the stent structure. The tubes can be flexible so that they can dramatically expand with a stent when a corresponding sheath is retracted.

Figure 48:
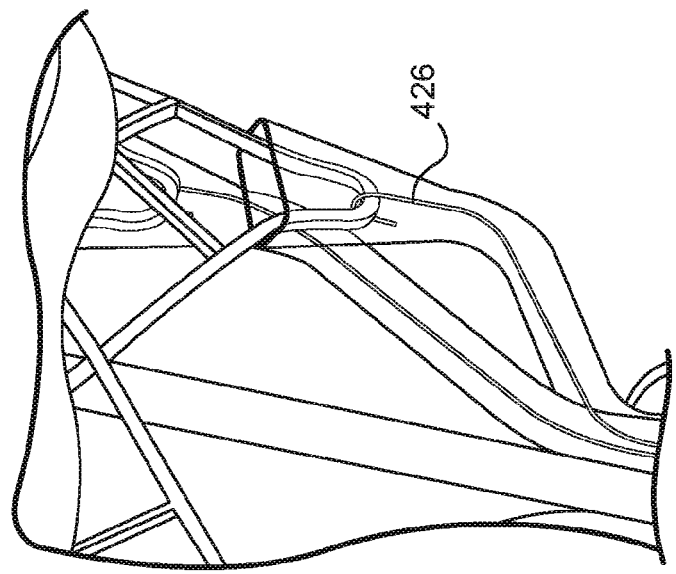
FIG. 48 is an enlarged view of a portion of the delivery system and stent of FIG. 47.
Figure 47:
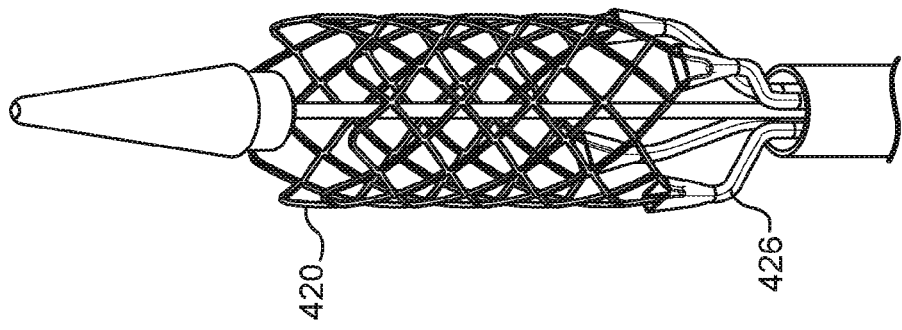
FIG. 47 is a perspective view of the stent of FIG. 46 being deployed in a prosthetic heart valve, with the stent being deployed yet remaining retrievable into the delivery system.
Figure 46:
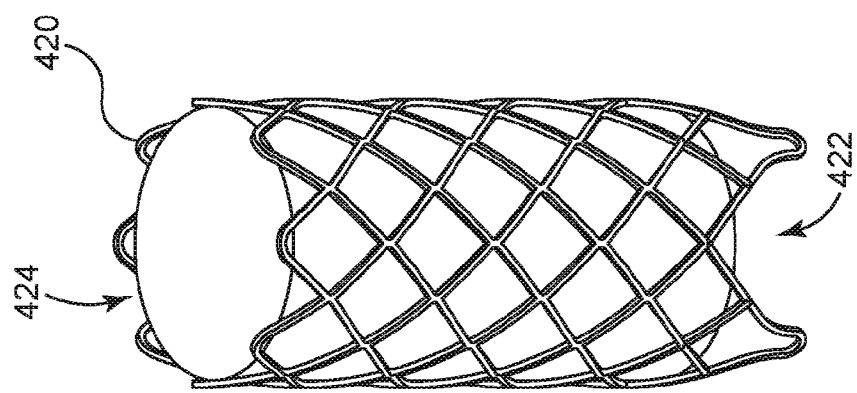
FIG. 46 is a perspective view of a stent that is retrievable after deployment in accordance with the invention.

FIGS. 46-48 illustrate another stent design for use with leaflets in a valved stent. In particular, a stent 420 is shown with a number of peaks or "V's" at both its inflow and outflow ends. The number of peaks may be the same at both ends of the stent, or as shown with stent 420, the two ends of the stent 420 may have a different number of peaks. In this embodiment, the end 422 has twice as many peaks as the end 424; however, the relative number of peaks at opposite ends of the stents can vary widely. In any case, either the inflow or the outflow petals or peaks are provided to interface with a delivery system, as shown in FIGS. 47 and 48. In that regard, the delivery system preferably includes some type of engagement device or structure (shown in this embodiment as wire hook-shaped structures 426) that facilitates full stent retrievability into the delivery system, even after the stent is partially or completely deployed. That is, as shown in FIG. 47, because the engagement devices remain engaged with the stent 420 after the stent is fully deployed from the sheath of a delivery system, the stent can be retracted back into the sheath, such as may be desirable if the stent cannot be positioned correctly in a patient. The various configurations discussed above relative to stent engagement alternatives can also be used with stent 420.

Figure 49:
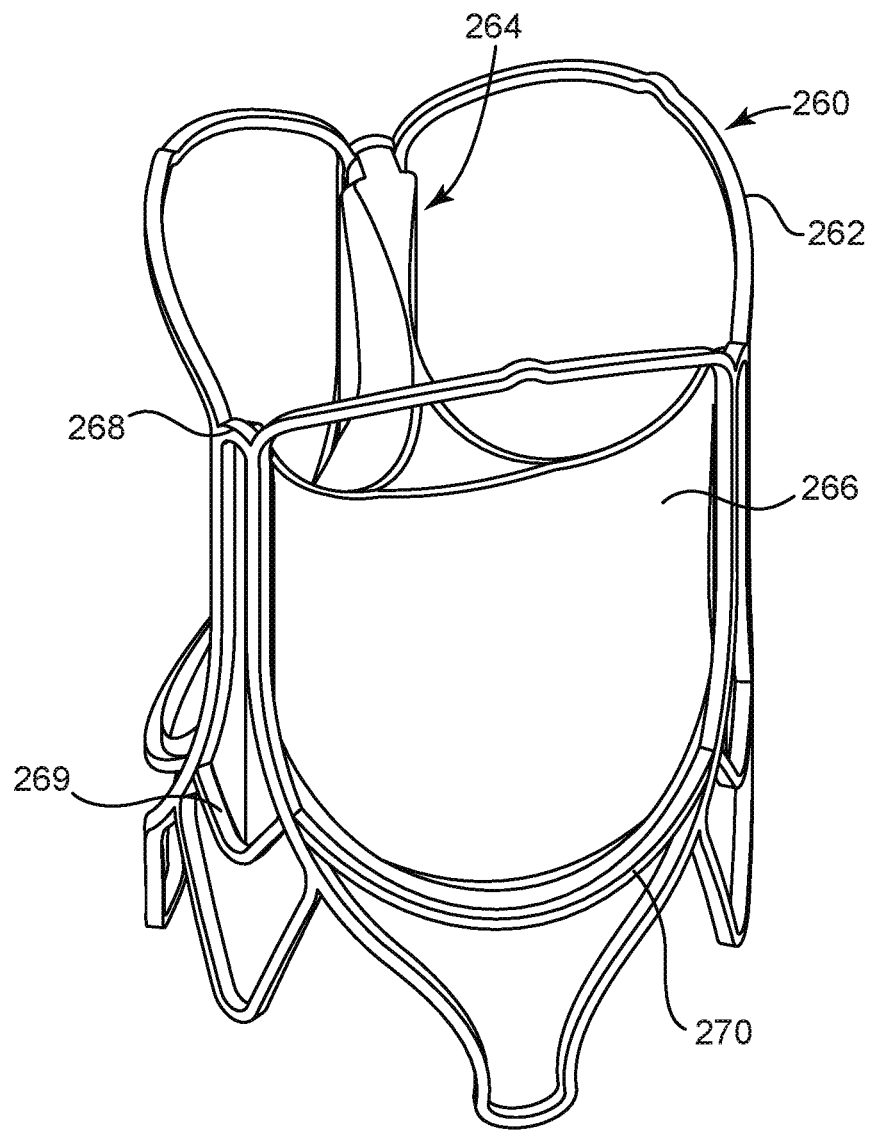
FIG. 49 is a perspective view of one exemplary embodiment of a replacement valve of the invention, which includes one exemplary stent structure along with a valve structure attached to the stent.

The delivery systems and methods described herein, along with other delivery systems and methods used for implantation of heart valves, can also be used with replacement heart valves that are not positioned within a previously implanted heart valve. FIG. 49 illustrates one such exemplary embodiment of a replacement heart valve 260, which comprises a stent 262 that is similar to stent 170 of FIG. 8; however, the stent 262 does not have the same flanges as the stent 170. It is noted that like this stent, any of the other embodiments of stents described herein could alternatively be provided without their respective flanges, which would allow the stents to additionally be used for replacement of a native valve. This figure further illustrates a leaflet structure 264 attached to the interior portion of stent 262. Leaflet structure 264 includes three leaflets 266, each of which has opposite side edges that are attached to one or both of upper vertical members 268 and lower vertical members 269 of stent 262. Stent 262 further includes lower connecting members 270 to which leaflet structure 264 can be attached via suturing, adhesives, or any known or developed method of providing such an attachment.

Figure 50:
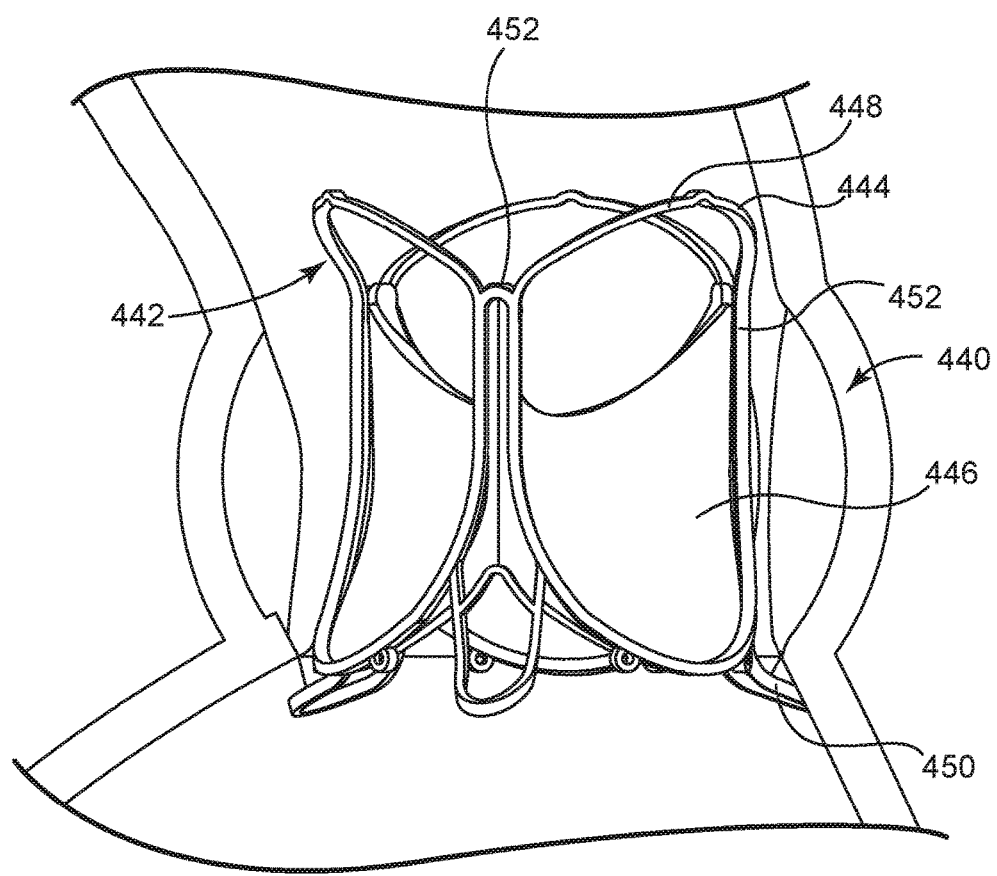
FIG. 50 is a cross-sectional perspective side view of a stented valve of the invention implanted into a native aorta.

FIG. 50 illustrates another stented valve 442 as positioned within a native aorta 440. This valve 442 can include a stent structure similar to those discussed herein relative to upper and lower flanges, extensions, and the like, such as stent 170 of FIG. 8, although it can vary in the positioning and configuration of the various structures. In general, stented valve 442 includes a stent 444 to which a tissue structure 446 is attached to provide the leaflets of the stented valve. Stent 444 includes upper connecting members 448 that can be used for engagement with a delivery system during the delivery and positioning process, and also includes lower flanges 450 that can serve as anchors with the native valve structure. It is noted that although the connecting members 448 of this stent structure and similar connecting members in other embodiments of the invention are shown as relatively simple curved structures, these connecting members can instead have a different structure that facilitates compression and expansion of the stent. For example, the connecting member could instead have a zigzag shape or structure or a coiled shape or structure. When implanted into a patient, the valve 442 can be aligned and oriented so that the portion of the tissue between extending vertical members 452 is aligned with the coronary arteries so that they are not blocked.

Figure 51:
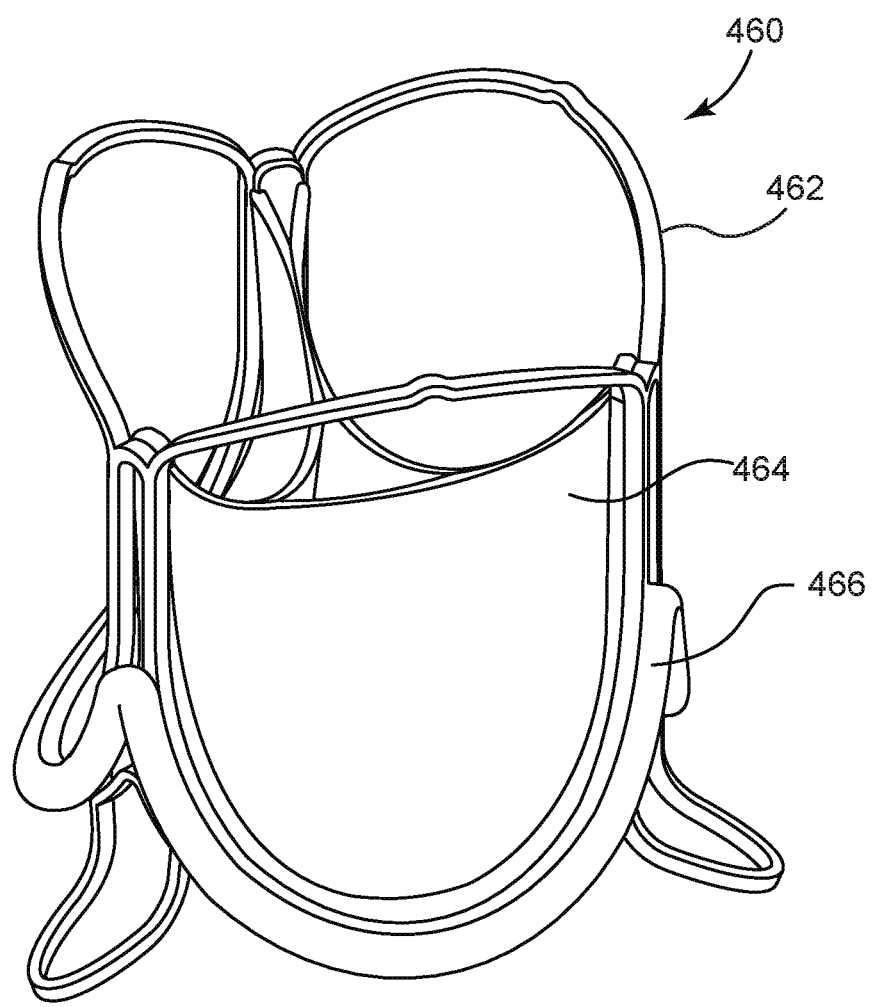
FIGS. 51 and 52 are perspective views of two embodiments of stented valves of the invention.
Figure 52:
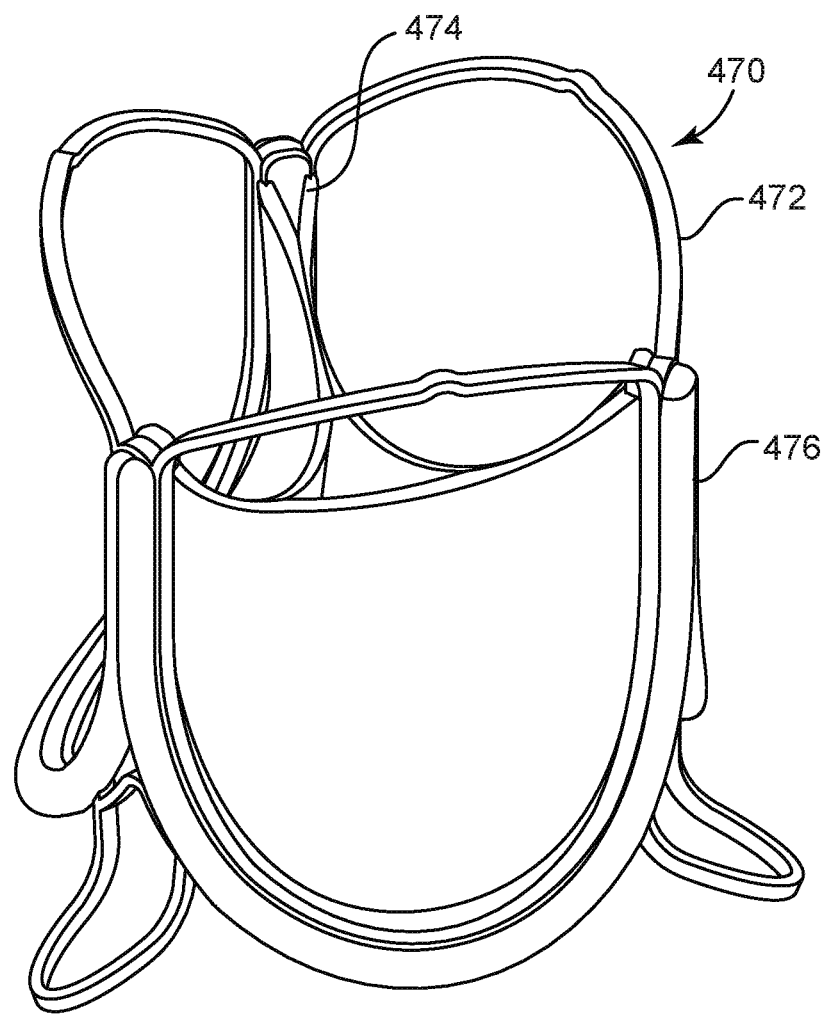

Stented valve 460 of FIG. 51 includes a stent structure 462 to which a tissue structure 464 is attached to provide the leaflets of the stented valve. Stented valve 460 further includes a seal or gasket 466 on the outer surface of the stent structure 462 to mitigate the possibility of paravalvular leakage when implanted in a patient. Stented valve 470 of FIG. 52 similarly includes a stent structure 472 to which a tissue structure 474 is attached to provide the leaflets of the stented valve. Stented valve 470 includes a seal or gasket 476 on the outer surface of the stent structure 472, wherein seal or gasket 476 extends higher along the stent rails than the gasket 466 of FIG. 51.

Figure 53:
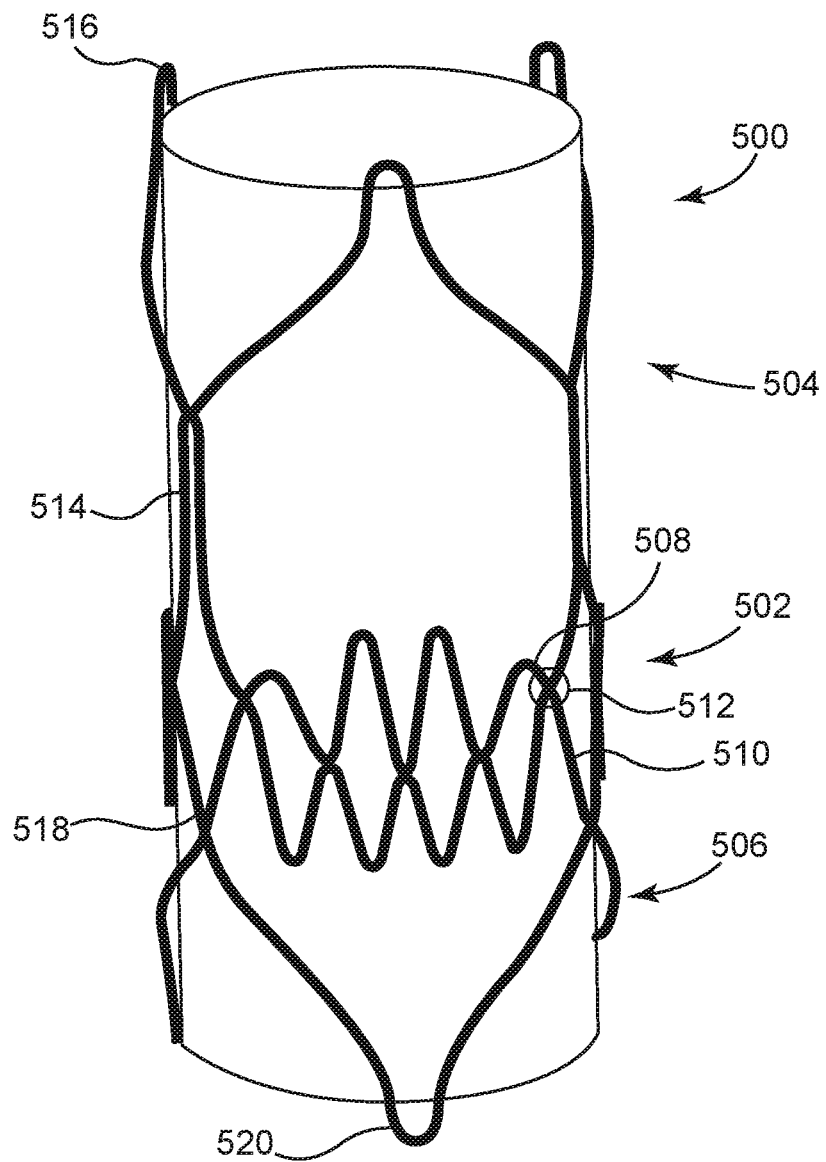
FIG. 53 is a front view of another embodiment of a stent of the invention as it can be used as a component of a replacement prosthetic heart valve.

FIG. 53 illustrates another stent design for use with leaflets in a stented valve. In particular, a stent 500 is shown with a central portion 502 from which a top structure 504 and a bottom structure 506 extend. Central portion 502 includes two sets of zigzag structures 508 and 510, each of which has a number of peaks and valleys or "V's" that are differently sized and shaped around the circumference of stent 500, although it is contemplated that the peaks and valleys can be the same around the circumference of the stent 500. In this embodiment, each of the peaks of the zigzag structure 510 is adjacent to a valley of the zigzag structure 508 such that they meet at an intersection point, such as is indicated at reference numeral 512. These intersection points 512 can provide attachment points for any tissue valve structures that may be positioned therein, if desired.

Structure 508 further optionally includes at least one extended peak 514 that is at least somewhat larger or higher than the other peaks in the structure, where this embodiment includes three of such extended peaks. The top structure 504 extends from these extended peaks 514 and is configured to provide at least one node 516 for attachment of the stent to a delivery device. In this embodiment, three nodes 516 are provided, although it is possible to have more or less than three nodes in such a stent structure. In a similar manner, structure 510 includes at least one peak 518, which is opposite the extended peaks 514 in this embodiment, from which the bottom structure 506 extends. The bottom structure 506 includes at least one node 520 for attachment of the stent 500 to a delivery device. Again, three nodes 520 are provided in this embodiment, although it is possible to have more or less than three nodes in such a stent structure. The number of nodes 516 may be the same or different than the number of nodes 520 in a particular stent structure. The nodes 516, 520 may be engageable with or attachable to some portion of a delivery system, such as the various delivery systems that are described herein.

Figure 56:
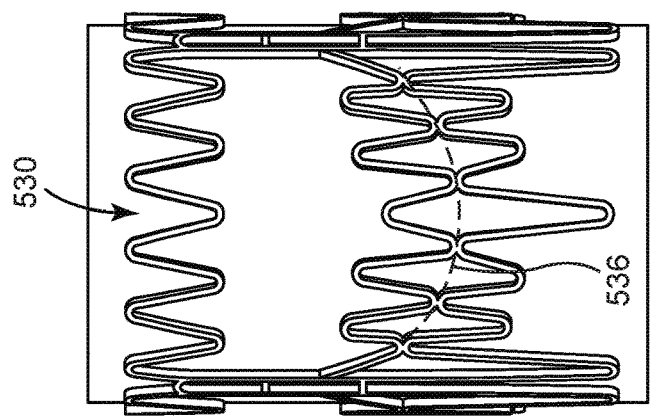
FIGS. 54-56 are front views of another stent embodiment of the invention.
Figure 55:
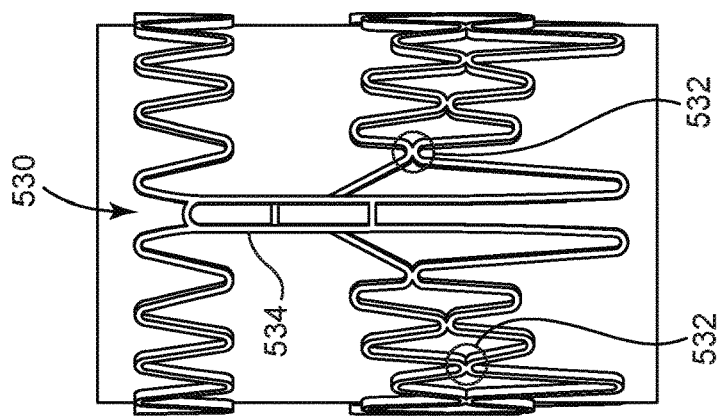
Figure 54:
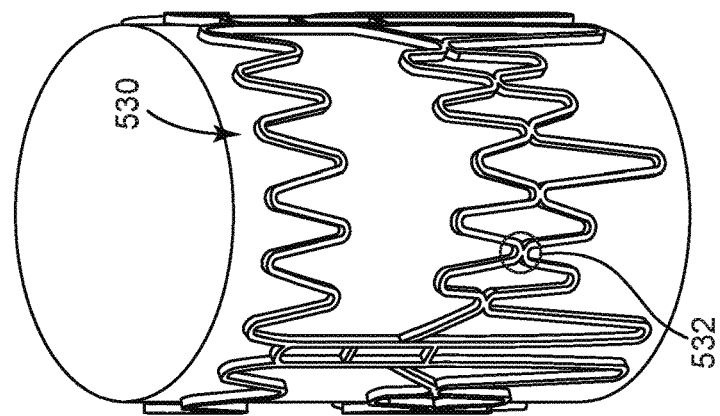

FIGS. 54-56 illustrate another stent design for use with leaflets as a stented valve. In particular, a stent 530 includes zigzag structures that extend from each other at a number of intersection points, such as intersection points designated by reference number 532. Again, the peaks and valleys of the multiple "V's" of the zigzag structures can vary somewhat from that shown, such as in the relative sizes, numbers, shapes and configurations of these structures. As shown in this embodiment, stent 530 includes a number of elongated portions 534 that generally extend from the top to the bottom of the stent 530, and three of such elongated portions 534 are provided in this embodiment to correspond with the number of commissures of a valve that can be attached to the stent. Alternatively, the stent may include more or less than three elongated portions 534. As with other embodiments of the stents of the invention, nodes 540 at one end of the stent 530 and nodes 542 at the opposite end of the stent 530 are configured in an arrangement that allows engagement of the nodes with a delivery system. The arrangement of the stent wires can desirably also push the native leaflets toward the vessel wall (e.g., the aortic wall) to minimize or eliminate interference between the native valves and those of the stented valve.

Figure 57:
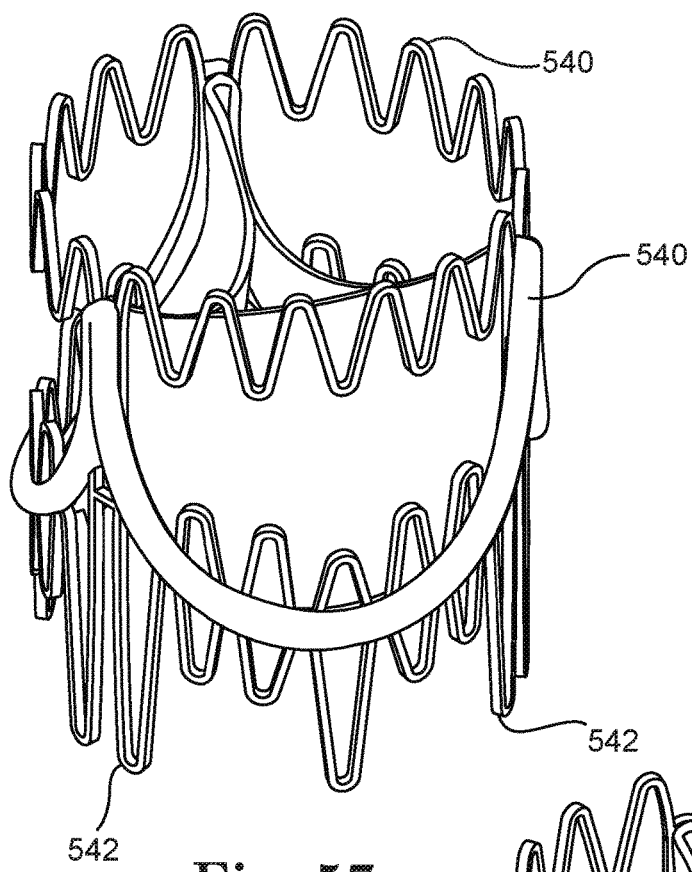
FIGS. 57 and 58 are perspective views of the stent of FIGS. 54-56 as a stented valve.
Figure 58:
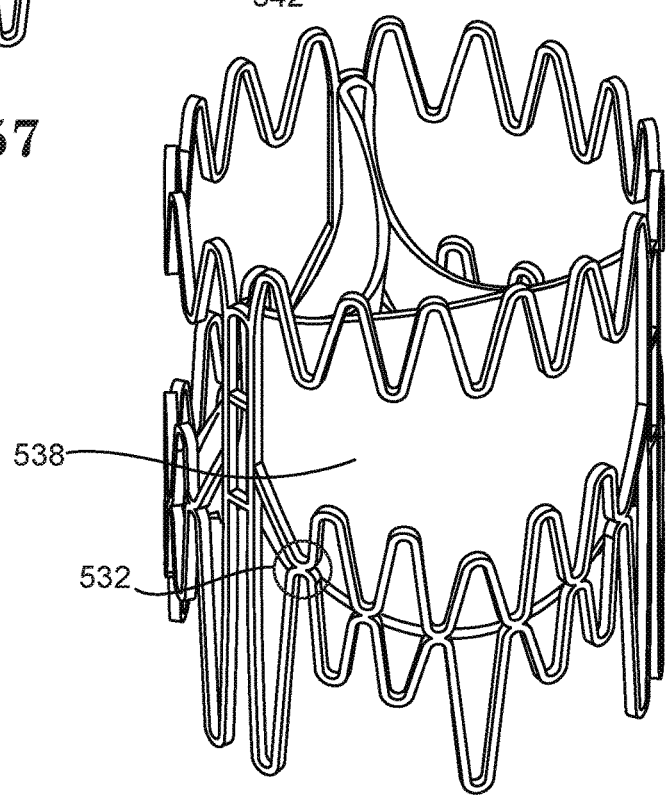

The intersection points 532 of stent 530 are arranged in such a way that they form a curve (indicated generally by broken line 536 in FIG. 56). Referring also to FIGS. 57 and 58, this curve can be designed to generally match the desired attachment points for a valve leaflet 538 that will be attached to the stent, such as by suturing. These intersection points 532, which are spaced from each other around the circumference of the stent 530, provide secure anchoring points to maintain the valve 538 in its desired position relative to the stent 530. In particular, these intersection points 532 can be advantageous to keep the valve in its desired location relative to the stent during compression and expansion of the stent. Stent 530 can further include a seal or gasket 540 on its outer surface to mitigate the possibility of paravalvular leakage when implanted in a patient.

As discussed herein, the various delivery systems of the invention can be used with any of the stent structures described herein, and/or with other stent structures, for replacement of a previously implanted prosthetic heart valve. A number of different stents and delivery systems can be used for such implantations, including the stents and delivery systems described above, along with other exemplary stents and delivery systems, such as those described in U.S. Patent Application Publication No. 2003/0199963-A1; U.S. patent application Ser. No. 12/070,347, entitled "REPLACEMENT PROSTHETIC HEART VALVES AND METHODS OF IMPLANTATION", filed on Feb. 15, 2008, U.S. paatent application Ser. No. 12/070,382, entitled "DELIVERY SYSTEMS AND METHODS OF IMPLANTATION FOR REPLACEMENT PROSTHETIC HEART VALVES", filed on Feb. 15, 2008; and U.S. patent application Ser. No. 12/070,387, entitled "REPLACEMENT PROSTHETIC HEART VALVES AND METHODS OF IMPLANTATION", filed on Feb. 15, 2008, all of which are incorporated by reference in their entireties.

Referring again to FIG. 1, the stent or valve structure 12 includes a sewing ring 14 and stent posts 16 and is covered by a covering 18, such as is included in the stented tissue valves commercially available from Medtronic, Inc. of Minneapolis, Minn. under the trade designations "Hancock II" and "Mosaic". A wide variety of other stented tissue valves, such as those described in U.S. Pat. Nos. 4,680,031, 4,892,541, and 5,032,128, the teachings of which are incorporated herein by reference, can be employed as the stent or valve structure 12. Alternatively, the structure 12 can be stentless, such as, for example, a Freestyle stentless bioprosthesis, commercially available from Medtronic, Inc. under the trade designation "Freestyle". Other acceptable stentless configurations are described in U.S. Pat. Nos. 5,156,621; 5,197,979; 5,336,258; 5,509,930; 6,001,126; 6,254,436; 6,342,070; 6,364,905; and 6,558,417, the teachings of which are incorporated herein by reference. Regardless, the leaflets (not shown) are attached to the structure 12 by sewing, crimping, adhesive, etc., for example, and can assume a variety of forms (e.g., autologous tissue, xenograph tissue, or synthetic material, such as polymers, metals, combinations thereof, and the like).

With any of the embodiments of the invention described herein, the valved stents can be placed inside of a failed valve with leaflets, as described herein, or the leaflets of the failed valve can be removed prior to delivery of the new valved stents, in accordance with known procedures for leaflet removal. Exemplary procedures for leaflet removal are described, for example, in U.S. Patent Publication No. 2004/0034380 (Woolfson et al.), and exemplary devices and methods of filtering in conjunction with leaflet removal are described, for example, in U.S. Pat. No. 6,896,690 (Lambrecht et al.) and U.S. Pat. No. 6,692,513 (Streeter et al.), all of which are incorporated herein by reference. In this way, the leaflets of the failed bioprosthesis cannot interfere with the leaflets of the newly implanted valved stent and particulates from the leaflet removal can be filtered from the blood of the patient.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A delivery device for delivering a replacement prosthetic heart valve to a native heart valve region of a patient, the delivery device comprising:
    an inner shaft;
    an outer sheath positioned around the inner shaft; wherein, in an extended position the outer sheath is configured to compressively retain the replacement prosthetic heart valve over the inner shaft and in a retracted position, the outer sheath is retracted proximally to expose the replacement prosthetic heart valve;
    a first engagement member having a distal end configured to engage the replacement prosthetic heart valve when the replacement prosthetic heart valve is positioned over the inner shaft; and
    a covering structure having a distal end and a proximal end;
    wherein a maximum dimension of the covering structure at the distal end is greater than a maximum dimension of the covering structure at the proximal end;
    and further wherein the covering structure has an extended position in which the covering structure covers the distal end of the first engagement member and a retracted position in which the covering structure is retracted proximally to expose the distal end of the first engagement member.

2. The delivery device of claim 1, wherein the distal end of the covering structure is tapered.

3. The delivery device of claim 1, wherein the first engagement member is configured to deform to release the replacement prosthetic heart valve from the delivery device.

4. The delivery device of claim 1, wherein the first engagement member has first and second portions extending from a common point, the first and second portions both configured to selectively engage and disengage the replacement prosthetic heart valve.

5. The delivery device of claim 1, wherein the first engagement member includes a protrusion that is configured to engage the replacement prosthetic heart valve.

6. The delivery device of claim 1, further comprising a second engagement member arranged to be selectively surrounded by the covering structure.

7. The delivery device of claim 1, wherein the first engagement member includes a delivery wire extending through the covering structure and configured to actuate release of the first engagement member from the replacement prosthetic heart valve from a delivery state in which the first engagement member is engaged with the replacement stented prosthetic heart valve to a full deployment state in which the first engagement member disengages the replacement stented prosthetic heart valve.

8. The delivery device of claim 1, wherein a cross-sectional shape of the distal end of the covering structure is generally rectangular.

9. A system for repairing a heart valve of a patient, the system comprising:
    a replacement prosthetic heart valve including:
        a self-expanding stent defining a proximal side opposite a distal side, and forming a first node at the proximal side, wherein the self-expanding stent is configured to self-expand from a compressed arrangement toward a normal, expanded arrangement,
    a valve structure attached to the self-expanding stent; and
    a delivery device including:
        an inner shaft,
        an outer sheath positioned around the inner shaft,
        a first engagement member having a distal end, and
        a covering structure at least partially surrounding the first engagement member, the covering structure having a distal end and a proximal end; wherein a maximum dimension of the covering structure at the distal end is greater than a maximum dimension of the covering structure at the proximal end;
    wherein the system is configured to provide:
        a delivery state in which the replacement prosthetic heart valve is loaded over the inner shaft and is retained in the compressed arrangement by the outer sheath, the delivery state further including the first engagement member engaging the first node and the covering structure surrounding the first engagement member at a location of connection between the first engagement member and the first node, wherein the delivery state further includes the covering structure disposed within the outer sheath, a partial deployment state in which the outer sheath is retracted from over the prosthetic heart valve, the partial deployment state further includes the first engagement member connected to the first node and the covering structure surrounding the first engagement member, the covering structure being partially retracted to expose the distal end of the first engagement member and the first node, and a full deployment state in which the replacement prosthetic heart valve is released from the delivery device.

10. The system of claim 9, wherein the distal end of the covering structure is tapered.

11. The system of claim 9, wherein the first engagement member is configured to deform in the full deployment state to release the replacement prosthetic heart valve from the delivery device.

12. The system of claim 9, wherein the first engagement member has first and second portions extending from a common point, the first and second portions configured to both engage the replacement prosthetic heart valve in the delivery state and disengage the replacement prosthetic heart valve in the full deployment state.

13. The system of claim 9, wherein the first engagement member includes a protrusion that is configured to engage the replacement prosthetic heart valve in the delivery state.

14. The system of claim 9, further comprising a second engagement member connected to a second node at the proximal side, the second engagement member surrounded by the covering structure in the delivery state.

15. The system of claim 9, wherein the first engagement member includes a delivery wire extending within the covering structure that can actuate release of the first engagement member from the replacement prosthetic heart valve from the delivery state to the full deployment state.

16. The system of claim 9, wherein a cross-sectional shape of the distal end of the covering structure is generally rectangular.

17. The system of claim 9, wherein the first engagement member has first and second portions that overlap each other at the first node.

18. The system of claim 9, wherein the first engagement member includes a hook-shaped structure.

* * * * *